United States Patent
Qin et al.

(10) Patent No.: US 10,308,594 B2
(45) Date of Patent: Jun. 4, 2019

(54) CURING AGENTS AND DEGRADABLE POLYMERS AND COMPOSITES BASED THEREON

(71) Applicant: ADESSO ADVANCED MATERIALS WUXI CO., LTD., Wuxi New District (CN)

(72) Inventors: Bing Qin, Shanghai (CN); Xin Li, Cottenham (GB); Bo Liang, Plainsboro, NJ (US)

(73) Assignee: Adesso Advanced Materials Wuhu Co., Ltd., Wuhu (CN)

( * ) Notice: Subject to any disclaimer, the term of this patent is extended or adjusted under 35 U.S.C. 154(b) by 321 days.

(21) Appl. No.: 14/781,242

(22) PCT Filed: Apr. 18, 2014

(86) PCT No.: PCT/CN2014/075698
§ 371 (c)(1),
(2) Date: Sep. 29, 2015

(87) PCT Pub. No.: WO2014/169847
PCT Pub. Date: Oct. 23, 2014

(65) Prior Publication Data
US 2016/0052871 A1 Feb. 25, 2016

(30) Foreign Application Priority Data

Apr. 18, 2013 (CN) .......................... 2013 1 0136022
Apr. 18, 2013 (CN) .......................... 2013 1 0137093
Apr. 18, 2013 (CN) .......................... 2013 1 0137251

(51) Int. Cl.
| | |
|---|---|
| B32B 27/26 | (2006.01) |
| B32B 27/38 | (2006.01) |
| B32B 27/04 | (2006.01) |
| C08G 59/50 | (2006.01) |
| C08J 5/24 | (2006.01) |
| C07C 43/30 | (2006.01) |
| C07C 235/00 | (2006.01) |
| C07C 235/08 | (2006.01) |
| C07C 243/00 | (2006.01) |
| C07C 243/24 | (2006.01) |
| C07C 243/26 | (2006.01) |
| C07C 243/28 | (2006.01) |
| C07C 243/38 | (2006.01) |
| C07C 217/84 | (2006.01) |
| C08J 11/16 | (2006.01) |
| C08J 11/26 | (2006.01) |
| C07C 201/12 | (2006.01) |
| C07C 213/02 | (2006.01) |
| C07C 241/02 | (2006.01) |
| C08G 59/14 | (2006.01) |
| C08K 7/06 | (2006.01) |
| C08L 63/00 | (2006.01) |
| C09J 9/00 | (2006.01) |
| C09J 163/00 | (2006.01) |

(52) U.S. Cl.
CPC .......... *C07C 243/38* (2013.01); *C07C 201/12* (2013.01); *C07C 213/02* (2013.01); *C07C 217/84* (2013.01); *C07C 241/02* (2013.01); *C07C 243/28* (2013.01); *C08G 59/1477* (2013.01); *C08G 59/50* (2013.01); *C08J 5/24* (2013.01); *C08J 11/16* (2013.01); *C08J 11/26* (2013.01); *C08K 7/06* (2013.01); *Y02W 30/705* (2015.05); *Y02W 30/706* (2015.05)

(58) Field of Classification Search
None
See application file for complete search history.

(56) References Cited

U.S. PATENT DOCUMENTS

| | | | | |
|---|---|---|---|---|
| 2,409,675 A | | 10/1946 | Gresham | |
| 2,765,304 A | * | 10/1956 | Siegrist | G03C 1/8155 252/589 |
| 4,935,502 A | * | 6/1990 | Kuhne | C09B 35/22 106/447 |

FOREIGN PATENT DOCUMENTS

| | | | | |
|---|---|---|---|---|
| CN | 103012747 A | | 4/2013 | |
| CN | 103193959 A | * | 7/2013 | ............. C08J 11/16 |
| JP | 5483046 A | | 7/1979 | |
| JP | 5579351 A | | 6/1980 | |
| JP | 6279370 A | | 10/1994 | |
| JP | 201152075 A | | 3/2011 | |

(Continued)

OTHER PUBLICATIONS

Kagaku "Synthesis of poly(hydrazide ethers) from hydroxybenzoic acids and their thermal cyclization" (Year: 1973).*

(Continued)

*Primary Examiner* — Michael J Feely
(74) *Attorney, Agent, or Firm* — Weisun Rao; Jun Chen; Venture Partner, LLC

(57) ABSTRACT

The present invention provides, among others, compounds of Formula (I) or a salt thereof, methods for making these compounds, degradable polymers and reinforced composites made therefrom, and methods for degrading and/or recycling the degradable polymers and reinforced composites.

(I)

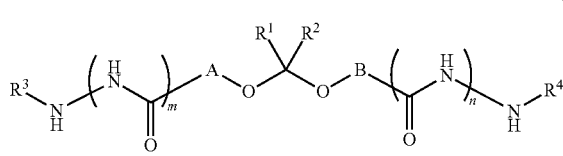

26 Claims, No Drawings

(56) References Cited

FOREIGN PATENT DOCUMENTS

| JP | 2011518784 A | 6/2011 |
|----|--------------|--------|
| JP | 2014507377 A | 3/2014 |
| WO | 2012071896 A1 | 6/2012 |
| WO | 2013007128 A1 | 1/2013 |

OTHER PUBLICATIONS

Machine Translation of CN 103193959 A (No Date).*
Translation of "Synthesis of Polyhydrazide Ethers From Oxybenzoic Acid and Their Thermal Cyclization Reaction" from "Kobunshi Kagaku", Ogata et al. (No date).*
Japanese office action in related application No. 2016-507998, dated Mar. 22, 2017, nine pages.
STN Registry of Compounds.
Korean office action in related application No. 10-2015-7032969, dated Mar. 22, 2017, twenty-nine pages.
Wojtkowski, Paul W., "Aromatic-Aliphatic Azomethine Ether Polymers and Fibers," Macromolecules, vol. 20, No. 4, pp. 740-748, Jul. 1, 1987.
Yang, Y. et al., "Preparation and Analysis of a Flexible Curing Agent for Epoxy Resin," Journal of Applied Polymer Science, vol. 114, No. 5, pp. 2706-2710, Jul. 16, 2009.

* cited by examiner

CURING AGENTS AND DEGRADABLE POLYMERS AND COMPOSITES BASED THEREON

CROSS-REFERENCE TO RELATED APPLICATIONS

This application is a U.S. national phase application of international application No. PCT/CN2014/075698, filed on Apr. 18, 2014, which claims priority to Chinese Application No. 201310137093.8, Chinese Application No. 201310136022.6, and Chinese Application No. 201310137251.X, all filed on Apr. 18, 2013, the contents of which are incorporated herein by reference in their entireties.

BACKGROUND OF THE INVENTION

Epoxy resin as binder and coating has a large global market, but as an industry standard plastic matrix of the manufacture of fiber-reinforced plastics (FRP). FRPs are composite materials composed by a polymer matrix and fibers such as carbon fibers, glass fibers, aramid fibers, natural fibers or other fibers. Fiber helps to enhance the strength, elasticity and other aspects of performance of plastics. FRPs are also commonly referred to as "plastic composite material," or simply as "composite material." "Plastic composite material" also includes non-fibrous materials such as metal or nanomaterials. Plastic composite material can be used as lightweight alternatives for other structural materials (such as steel or aluminum), which are widely used in automotive, aerospace, marine craft, wind energy, and sporting goods industries. Lightweight composite material help to improve energy efficiency, which has significant environmental benefits, however, the persistence and limits of recycling of thermoset plastic composite material in the environment offset its positive impact. On the growing wind power can be predicted to cause accumulation of garbage of industrial waste materials will be a typical example.

The most common epoxy resin formula contains a diepoxide resin (resin) and the polyamine compound (curing agent), essentially may form infinite molecular weight, cross-linked polymer network structure. The combination of "resin" and "curing agent" is sometimes referred to as "cured epoxy resin", "cured resin" or simply called "resin" or "epoxy resin." The wide range of applications of epoxy resin formula of the composite material is due to its excellent processability before curing properties and excellent adhesion, mechanical strength, thermal dispersion, electrical properties, chemical resistance after curing. In addition, high density and three-dimensional network structure of the epoxy resin after curing make it extremely hard and durable material that can withstand a wide range of environmental conditions' influence. Meanwhile, the cross-linked structure of cured epoxy resin makes it particularly difficult to remove, recycling and reuse. Essentially, the crosslinking reaction of a polyamine compound with an epoxy resin usually is irreversible, and therefore this material cannot be re-melting, not lossless re-formed and easily dissolved. Degradable latent epoxy resin curing agents are research focus of epoxy resin curing agent home and abroad in recent years. Latent curing agent, is the curing agent added to the epoxy resin and its constituent one-component system have a certain storage stability at the room temperature, and in the heat, light, moisture, pressure and other conditions can quickly curing react. Compared to widely used two-component epoxy resin system nowadays, one-component epoxy resin system mixing prepared by the latent curing agent and epoxy resin has advantages of simplified production operation process, no environmental pollution, large-scale industrial production applications. The research of latent epoxy curing agent are mainly by physical or chemical methods, to improve the curing activity of the general use of low and high temperature curing agent, one is sealing off and passivating the reactivity of some curing agent with high reactivity but poor storage stability, Another is improving and inspiring the reactivity of some curing agent with high storage stability but poor reactivity, Ultimately, make the curing agent have certain storage stability after added to the epoxy resin at room temperature, while using will achieve the purpose of rapid curing by light, heat and other external conditions to release the reactivity of the curing agent.

Epoxy prepreg is a compound system composed of epoxy resin, curing system and the reinforcing fiber, the resin system was an uncured state as an intermediate substrate for preparing the composite. Carbon fiber composite material prepared by the epoxy prepreg has high specific strength and specific modulus, devisable performance and diversity of forming technology, which is widely used in construction materials, aerospace and civilian entertainment.

By 2015, global composites production capacity will significantly increase, and exceed 10 million tons. However, how to deal with and recycle the waste of fiber composites have hindered its booming as a worldwide problem, thereby constraining the sustainable development of fiber composites.

The recovery process of fiber composites have been reported roughly in three ways: landfill, incineration and grinding. Landfilling is burying waste composite materials into the ground directly, which is simple, low cost, but occupy the land and pollution remains the same. While incineration can recover some energy, but the incineration process requires a lot of energy, also it is a problem from environmental point of view. A novel carbon fiber composite material recycling technology allows the plastic matrix composite material to remove by a special incinerator and the residual carbon fibers may be recovered for reuse. Although this approach steps to the direction of the sustainable development, it does not represent completely recycling because the plastic matrix is destroyed during the recycling process and cannot be recycled. Through pulverizing recovering method, the obtained fiber material is reused as additional materials, but if added to a certain percentage, it will reduce related mechanical properties of materials. In general, these methods have their limitations in varying degrees, existing disadvantages of fiber shortening, performance degradation, environmental pollution, and high recycling cost and so on, therefore, effective and feasible method for the recycling of waste composite materials is still a issue to be addressed in composites field.

SUMMARY OF THE INVENTION

Aiming at the problems of the existing technology, this invention provides, among others, compounds and salts thereof that can be used as degradable latent epoxy curing agents, methods for synthesizing these compounds and salts, synthetic polymer and reinforced composite materials derived from these compounds or salts as curing agent and epoxy resin, methods for degrading the polymer and reinforced composite materials. The prepared degradable reinforced composite materials provided by this invention have good storage stability of more than one month storage period at the room temperature, and at higher temperature, it can be quickly cured; under certain conditions, the composite material is degraded, and the matrix degradation products of reinforcing material and epoxy resin can be separated and recovered. Furthermore, the degradation and recovery method of reinforced composite material is economic, easy to control and can proceed in relatively mild reaction conditions.

Accordingly, in one aspect, the invention provides a compound of Formula (I) or a salt thereof:

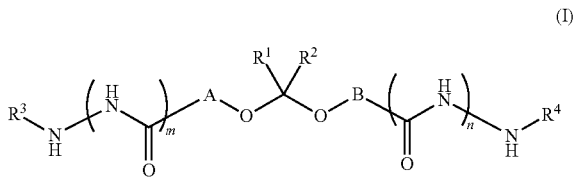

(I)

In Formula (I), each of $R^1$ and $R^2$, independently, is hydrogen, alkyl, cycloalkyl, heterocyclic, heterocycloalkyl, alkenyl, cycloalkenyl, aryl, heteroaryl, alkyl-hetero-alkyl, alkynyl, alkylene, alkylene-hetero-alkylene, alkenylene, alkylene-hetero-alkenylene, alkynylene, or alkylene-hetero-alkynylene; or, $R^1$ and $R^2$, together with the carbon atom to which they are attached, form a 3- to 7-membered saturated or unsaturated cyclic or heterocyclic ring containing 1 to 3 heteroatoms each independently being O, S, or NH;

each of A and B, independently, is alkylene, alkylene-hetero-alkylene, alkenylene, alkenylene-hetero-alkenylene, alkylene-hetero-alkenylene, alkynylene, cycloalkylene, alkylene-cycloalkylene, alkylene-cycloalkylene-alkylene, alkenylene-cycloalkylene, alkenylene-cycloalkylene-alkenylene, alkylene-cycloalkylene-alkenylene, alkynylene-cycloalkylene, alkynylene-cycloalkylene-alkynylene, heterocycloalkylene, alkylene-heterocycloalkylene, alkylene-heterocycloalkylene-alkylene, alkenylene-heterocycloalkylene, alkenylene-heterocycloalkylene-alkenylene, alkylene-heterocycloalkylene-alkenylene, alkynylene-heterocycloalkylene, alkynylene-heterocycloalkylene-alkynylene, cycloalkenylene, alkylene-cycloalkenylene, alkylene-cycloalkenylene-alkylene, alkenylene-cycloalkenylene, alkenylene-cycloalkenylene-alkenylene, alkylene-cycloalkenylene-alkenylene, alkynylene-cycloalkenylene, alkynylene-cycloalkenylene-alkynylene, heterocycloalkenylene, alkylene-heterocycloalkenylene, alkylene-heterocycloalkenylene-alkylene, alkenylene-heterocycloalkenylene, alkenylene-heterocycloalkenylene-alkenylene, alkylene-heterocycloalkenylene-alkenylene, alkynylene-heterocycloalkenylene, alkynylene-heterocycloalkenylene-alkynylene, arylene, alkylene-arylene, alkylene-arylene-alkylene, alkenylene-arylene, alkenylene-arylene-alkenylene, alkylene-arylene-alkenylene, alkynylene-arylene, alkynylene-arylene-alkynylene, heteroarylene, alkylene-heteroarylene, alkylene-heteroarylene-alkylene, alkenylene-heteroarylene, alkenylene-heteroarylene-alkenylene, alkylene-heteroarylene-alkenylene, alkynylene-heteroarylene, or alkynylene-heteroarylene-alkynylene;

each of $R^3$ and $R^4$, independently, is hydrogen, alkyl, cycloalkyl, heterocyclic, heterocycloalkyl, alkenyl, cycloalkenyl, aryl, heteroaryl, alkoxyalkyl, or alkynyl; and each of m and n, independently, is 0 or 1.

In some embodiments, both m and n are 0.

In some other embodiments, both m and n are 1.

In some embodiments, each of A and B, independently, is alkylene, alkenylene, arylene, alkylene-arylene, alkenylene-arylene, alkynylene-arylene, heteroarylene, alkylene-heteroarylene, alkenylene-heteroarylene, or alkynylene-heteroarylene.

In some embodiments, each of A and B, independently, is alkylene or arylene. As examples, both A and B are, at the same time, alkylene or arylene (e.g., methylene, ethylene, or phenylene).

In some embodiments, each of $R^1$ and $R^2$, independently, is hydrogen, alkyl, cycloalkyl, heterocyclic, heterocycloalkyl, alkenyl, cycloalkenyl, aryl, heteroaryl, alkyl-hetero-alkyl, alkynyl, alkylene, alkylene-hetero-alkylene, alkenylene, alkylene-hetero-alkenylene, alkynylene, or alkylene-hetero-alkynylene; or $R^1$ and $R^2$, together with the carbon atom to which they are attached, form a 3- to 7-membered saturated or unsaturated ring.

In some embodiments, each of $R^1$ and $R^2$, independently, hydrogen or alkyl, or $R^1$ and $R^2$, together with the carbon atom to which they are attached, form a 3- to 7-membered saturated ring. For example, each of $R^1$ and $R^2$, independently, is hydrogen, methyl, or ethyl.

In some embodiments, each of $R^1$ and $R^2$, independently, is preferably hydrogen, $C_{1-12}$ alkyl, $C_{3-12}$ cycloalkyl, $C_{6-12}$ aryl, $C_{3-11}$ heteroaryl, more preferably a hydrogen, $C_{1-6}$ alkyl, $C_{4-6}$ cycloalkyl, $C_{6-10}$ aryl, $C_{3-8}$ heteroaromatic most preferably a hydrogen, methyl, ethyl, propyl, isopropyl, butyl, isobutyl, tert-butyl; or $R^1$ and $R^2$, together with the carbon atom to which they are attached, form 3- to 7-membered saturated ring.

In some embodiments, each of A and B, independently, is preferably $C_{1-8}$ alkenylene, $C_{2-12}$ alkylene-hetero-alkylene, or $C_{4-15}$ alkenylene heterocycloalkylene-alkenylene, more preferably a $C_{1-8}$ alkenylene, $C_{2-8}$ alkylene-heteroalkylene, or $C_{4-10}$ alkenyiene-heterocycloalkylene alkenylene, most preferably a vinylene propenylene.

In some embodiments, each of $R^3$ and $R^4$, independently, is hydrogen or alkyl (e.g., hydrogen, methyl, ethyl, propyl, or isopropyl).

In some embodiments, the compound is

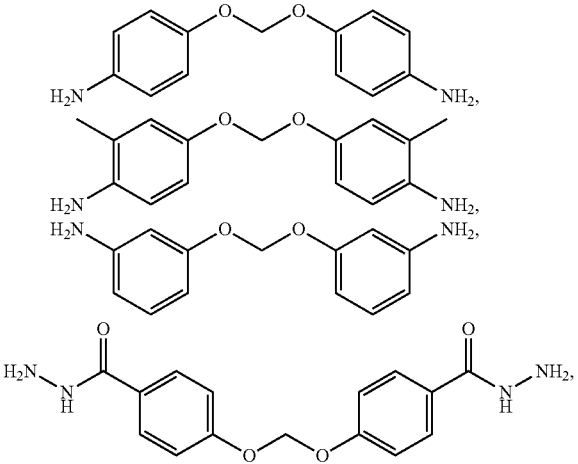

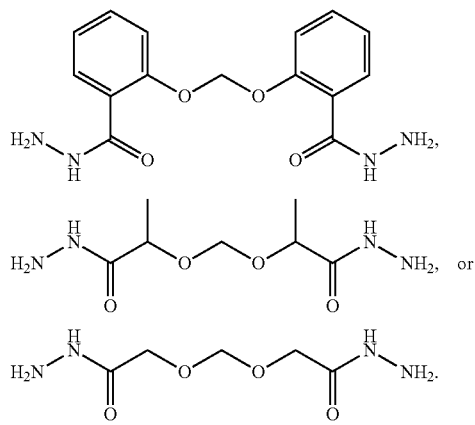

In some embodiments the compound is a salt formed with an organic acid or Lewis acid. The organic acid, e.g., can be a $C_{1-10}$ aliphatic, cycloaliphatic, aromatic, or heteroaromatic carboxylic acid Examples of the salts include those containing lactate ion, oxalic ion, malate ion, tartrate ion, adipate ion, suberate ion, benzoate ion, phthalate ion, malonate ion, succinate ion glutarate ion, pimelate ion, acetate ion isophthalate ion, salicylate ion. Examples of Lewis acid include zinc chloride, aluminium chloride, ferric chloride, niobium chloride, boron trifluoride, and trifluoromethanesulfonate, in lanthanide.

Specific examples of such salts include oxalate, citrate, or zinc chloride, More specific examples of such salts include:

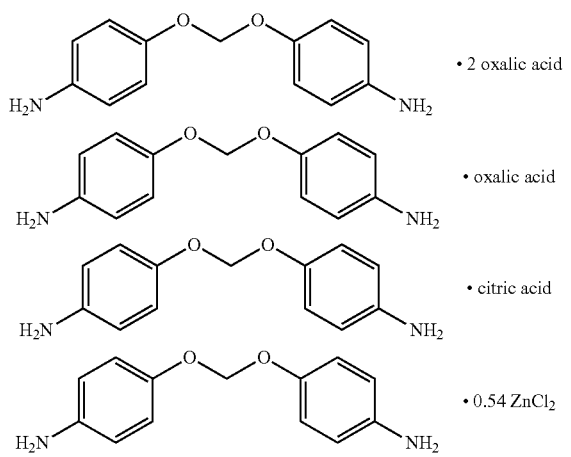

Another aspect of this invention provides a degradable cross-linked polymer, wherein the polymer is synthesized by curing an epoxy resin with a compound described above (as a curing agent), the epoxy resin comprises a glycidyl ether epoxy resin, glycidyl ester epoxy resin, glycidyl amine epoxy resin, trifunctional epoxy resin, tetrafunctional epoxy resin, novolac epoxy resin, cresol-novolac epoxy resin, aliphatic epoxy resin, alicyclic epoxy resin, or nitrogen-containing epoxy resin.

The cross-linked polymer comprises a breakable cross-linked structure of the following formula:

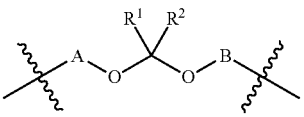

In this formula, each of $R^1$ and $R^2$, independently, is hydrogen, alkyl, cycloalkyl, heterocyclic, heterocycloalkyl, alkenyl, cycloalkenyl, aryl, heteroaryl, alkyl-hetero-alkyl, alkynyl, alkylene, alkylene-hetero-alkylene, alkenylene, alkylene-hetero-alkenylene, alkynylene, or alkylene-hetero-alkynylene; or $R^1$ and $R^2$, together with the carbon atom to which they are attached, form a 3-7 membered ring, and each of A and B, independently, is respectively arylene, alkylene-arylene, alkenylene-arylene, alkynylene-arylene, heteroarylene, alkylene-heteroarylene, alkenylene-heteroarylene, or alkynylene-heteroarylene; or each A and B, independently, is alkylene, alkylene-hetero-alkylene, alkenylene, alkenylene-hetero-alkenylene, alkylene-hetero-alkenylene, alkynylene, cycloalkylene, alkylene-cycloalkylene, alkylene-cycloalkylene-alkylene, alkenylene-cycloalkylene, alkenylene-cycloalkylene-alkenylene, alkylene-cycloalkylene-alkenylene, alkynylene-cycloalkylene, alkynylene-cycloalkylene-alkynylene, heterocycloalkylene, alkylene-heterocycloalkylene, alkylene-heterocycloalkylene-alkylene, alkenylene-heterocycloalkylene, alkenylene-heterocycloalkylene-alkenylene, alkylene-heterocycloalkylene-alkenylene, alkynylene-heterocycloalkylene, alkynylene-heterocycloalkylene-alkynylene,
cycloalkenylene, alkylene-cycloalkenylene, alkylene-cycloalkenylene-alkylene, alkenylene-cycloalkenylene, alkenylene-cycloalkenylene-alkenylene, alkylene-cycloalkenylene-alkenylene, alkynylene-cycloalkenylene, alkynylene-cycloalkenylene-alkynylene, heterocycloalkenylene, alkylene-heterocycloalkenylene, alkylene-heterocycloalkenylene-alkylene, alkenylene-heterocycloalkenylene, alkenylene-heterocycloalkenylene-alkenylene, alkylene-heterocycloalkenylene-alkenylene, alkynylene-heterocycloalkenylene, alkynylene-heterocycloalkenylene-alkynylene, arylene, alkylene-arylene, alkylene-arylene-alkylene, alkenylene-arylene, alkenylene-arylene-alkenylene, alkylene-arylene-alkenylene, alkynylene-arylene, alkynylene-arylene-alkynylene, heteroarylene, alkylene-heteroarylene, alkylene-heteroarylene-alkylene, alkenylene-heteroarylene, alkenylene-heteroarylene-alkenylene, alkylene-heteroarylene-alkenylene, alkynylene-heteroarylene, alkynylene-heteroarylene-alkynylene.

Still another aspect of this invention provides a prepreg material or a reinforced composite material, wherein the material is derived from a compound described above (as a curing agent), an epoxy resin, an optional auxiliary material, and a reinforcing material; the epoxy resin comprises a glycidyl ether epoxy resin, glycidyl ester epoxy resins, glycidyl amine epoxy resin, trifunctional epoxy resin, tetrafunctional epoxy resin, novolac epoxy resin, o-cresol novolac epoxy resin, aliphatic epoxy resin, alicyclic epoxy resin, or nitrogen-containing epoxy resin; the reinforcing material comprise carbon nanotubes, boron nitride nanotubes, carbon black, metal nano-particles, metal oxide nanoparticles, organic nanoparticles, iron oxide, glass fibers, carbon fibers, natural fibers, synthetic fibers, or a fabric made up by fiber material; and the optional auxiliary material comprise an accelerator, diluent, plasticizer, toughening agent, thickening agent, coupling agent, defoamer, flatting agent, ultraviolet absorber, antioxidant, brightener, fluorescent agent, pigment, or filler.

The reinforced composite material is produced by the method of prepreg molding. As an illustration of the principal of prepreg molding, fabrics and fibers are pre-impregnated, under heat and pressure or with solvent, with a pre-catalysed resin. The catalyst is largely latent at ambient temperatures giving the materials several weeks, or sometimes months, of useful life when defrosted. However to prolong storage life the materials are stored frozen. The resin is usually a near-solid at ambient temperatures, and so the pre-impregnated materials (prepregs) have a light sticky feel to them, such as that of adhesive tape. Unidirectional materials take fiber direct from a creel, and are held together by the resin alone. The prepregs are laid up by hand or machine onto a mould surface, vacuum bagged and then heated to typically 120-180° C. This allows the resin to initially reflow and eventually to cure. Additional pressure for the moulding is usually provided by an autoclave (effectively a pressurised oven) which can apply up to 5 atmospheres to the laminate.

A further aspect of this invention provides a method for degrading degradable cross-linked polymer or reinforced composite material as described above. The method includes the steps of:
  (1) under the condition of heating and stirring, the cross-linked polymer or reinforced composite material is immersed in a mixture comprising an acid and a solvent, the mixture is heated to a temperature in the range of 15-400° C., the heating time is 1-120 hours, and the mass concentration of acid in the solvent is 0.1-100%;
  (2) using an alkaline solution of 0-200° C. to adjust the pH value of the mixture of acid and solvent to at least 6, the mass concentration of alkali solution is 0.1-100%.

In some embodiments, the acid comprises hydrochloric acid, hydrobromic acid, hydrofluoric acid, acetic acid, trifluoroacetic acid, lactic acid, formic acid, propionic acid, citric acid, methanesulfonic acid, p-toluenesulfonic acid, nitric acid, sulfuric acid, sulfurous acid, phosphoric acid, perchloric acid, benzoic acid, salicylic acid, or phthalic acid; the solvent comprises methanol, ethanol, ethylene glycol, propanol, isopropanol, butanol, isobutanol, t-butanol, pentanol, hexanol, heptanol, octanol, nonanol, benzyl alcohol, phenethyl alcohol, p-hydroxymethyl benzene, m-hydroxymethyl benzene, o-hydroxy benzene, p-hydroxyethyl benzene, m-hydroxyethyl benzene, o-hydroxyethyl benzene, water, N, N-dimethylformamide, N, N-dimethylacetamide, N-methylpyrrolidone, dimethyl sulfoxide, tetrahydrofuran, methyl tetrahydrofuran, glycerol, or dioxane; the alkali comprises lithium hydroxide, sodium hydroxide, potassium hydroxide, calcium hydroxide, sodium carbonate, sodium bicarbonate, potassium carbonate, potassium bicarbonate, ammonia; the alkali solvent comprises methanol, ethanol, ethylene glycol, propanol, isopropanol, butanol, isobutanol, t-butanol, pentanol, hexanol, heptanol, octanol, nonanol, water, N, N-dimethylformamide, N, N-dimethylacetamide, N-methylpyrrolidone, dimethyl sulfoxide, tetrahydrofuran, methyl tetrahydrofuran, glycerol, or dioxane.

In some other embodiments, in step (1), the heating temperature is 80-150° C., heating time is 4-8 hours, and the mass concentration of acid in the solvent is 0.5-20%; in step (2) the temperature is 5-50° C., the pH value is adjusted to the range of 6-12, the concentration of alkali solution is 5-30%.

Degradable epoxy matrix (i.e., the degradable cross-linked polymer polymerized by curing agent and epoxy resin systems) may combine with glass fibers, carbon fibers, natural fibers, synthetic fibers, or other fiber material for preparing degradable epoxy resin prepreg, and also with non-fiber-reinforced materials, such as carbon nanotubes, boron nitride nanotubes, carbon black, metal nano-particles, metal oxide nanoparticles, organic nanoparticles, iron oxide, or other non-fibrous materials for preparing degradable epoxy prepreg. Degradable epoxy prepreg composite material can be prepared into degradable epoxy composites through the standard operating.

Furthermore, the principle of degradation of reinforced composite material: immerse composite material into the hot recovery solution of acid and solvent. Firstly, the epoxy matrix is degraded, and then separated the received reinforcements, and finally recycled by alkali neutralization. Under such conditions, the epoxy matrix can be degraded for its acid-sensitive cross-linked structure, in which the acetal bond will break resulting in cross-linked structure of epoxy resin matrix to dissolve into the non-cross-linked polymer which is soluable in the organic solvent (e.g., thermoplastic resin). When epoxy matrix is fully dissolved, the fiber can be removed from the solution, and the solution after neutralization by alkali, sedimentation, the epoxy matrix degradation products can be solid-liquid separated and recovered. Recycled reinforcements and non-cross-linked polymers all can be separated, recovered and reused.

Yet still another aspect of this invention provides a method for preparing a compound of Formula (I) as described above, wherein both m and n are 0, both $R^3$ and $R^4$ are hydrogen. This method includes the steps as depicted in the following scheme:

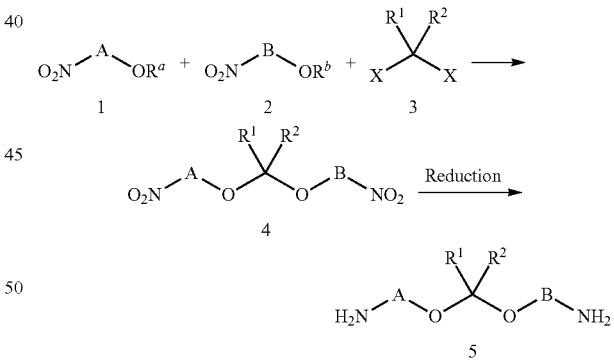

wherein
  A, B, $R^1$, and $R^2$ are as defined above;
  each X independently is a halogen atom;
  each of $R^a$ and $R^b$, independently, is hydrogen, alkali metal, alkaline-earth metal, or quaternary ammonium salt.

In some embodiments, each of $R^1$ and $R^2$ independently is hydrogen, alkyl, cycloalkyl, heterocyclic, heterocycloalkyl, alkenyl, cycloalkenyl, aryl, heteroaryl, alkyl-hetero-alkyl, alkynyl, alkylene, alkylene-hetero-alkylene, alkenylene, alkylene-hetero-alkenylene, alkynylene, alkylene-hetero-alkynylene; or $R^1$ and $R^2$, together with the carbon atom to which they are attached, form a 3-7 membered ring; each of $R^3$ and $R^4$, independently, is hydrogen, alkali metal, alkaline earth metal, or quaternary ammonium salt; each A and B, independently, is respectively arylene, alkylene-arylene, alkenylene-arylene, alkynylene-arylene, heteroarylene, alkylene-heteroarylene, alkenylene-heteroarylene, alkynylene-heteroarylene;

In some embodiments of the method, the first step forming the dinitro intermediate (compound 3) takes place in an organic solvent at a temperature between 30 and 200° C.; and the reduction reaction takes place at a temperature between 20-150° C. The organic solution can include N,N-dimethylformamide, dimethyl sulfoxide, tetrahydrofuran, or dioxane; and the reduction reaction is hydrazine reduction, catalytic hydrogenation, metal reduction, or sulfide reduction.

The hydrazine reduction refers to procedure in which, the intermediate (compound 4) dissolves in the mixed system combined by organic solvent and hydrazine hydrate or anhydrous hydrazine, and forms compound 5 which is a degradable organic aromatic amines curing agent.

In a catalytic hydrogenation reaction, the catalyst is at least one of Pd/C, Pt/C, ferric chloride hexahydrate, ferric chloride, ferric oxide, magnesium oxide, the organic solvent is at least one of methanol, ethanol, propanol, isopropanol, butanol, isobutanol, t-butanol, pentanol, hexanol, heptanol, octanol, nonanol, decanol, dioxane, tetrahydrofuran, ethylene glycol, and the reaction temperature is 20-150° C.

In yet still another aspect, the present invention provides a method as depicted below for preparing a compound of Formula (I) described above, wherein both m and n are 1, both $R^3$ and $R^4$ are hydrogen.

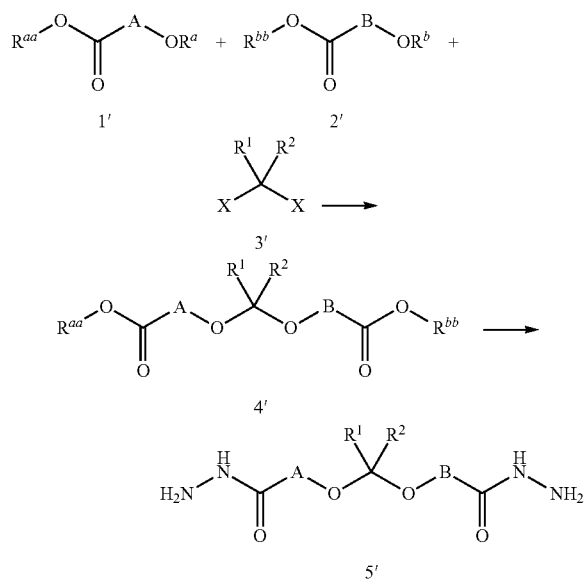

In the Scheme shown above,
A, B, $R^1$, and $R^2$ are as defined above,
each X independently is a halogen atom, or both X groups together form =O;
each of $R^{aa}$ and $R^{bb}$, independently, is alkyl, cycloalkyl, heterocycle, heterocycloalkyl, alkenyl, cycloalkenyl, aryl, heteroaryl, alkyl-hetero-alkyl, or alkynyl; and
each of $R^a$ and $R^b$, independently, is hydrogen, alkali metal, alkaline earth metal, or quaternary ammonium salt.

In some embodiments, each X independently is a halogen atom, compounds 1', 2', and 3' react in a first organic solvent at a temperature in the range of 30-200° C. to produce intermediate 4', the molar ratio of compounds 1' and 2' is not higher than 10:1, and the molar ratio of the compounds 1' and 2' versus compound 3' is not higher than 100:1.

In some embodiments, the first organic solvent comprises tetrahydrofuran or dioxane.

In some embodiments, each X independently is a halogen atom, intermediate compound 4' reacts with hydrazine in a second organic solvent at a temperature in the range of 0-150° C. to produce compound 5'.

In these embodiments, the second organic solvent comprises methanol, ethanol, propanol, isopropanol, butanol, isobutanol, t-butanol, pentanol, hexanol, heptanol, octanol, nonanol, decanol, dioxane, tetrahydrofuran, or ethylene glycol; and the hydrazine comprises anhydrous hydrazine or hydrazine hydrate.

In some embodiments, both X groups together form =O, and both $R^a$ and $R^b$ are hydrogen.

In some embodiments, both X groups together form =O, and both $R^a$ and $R^b$ are hydrogen, compounds 1', 2', and 3' react in a first organic solvent in the presence of a catalyst at a temperature in the range of 30-200° C. to produce intermediate 4', the molar ratio of compounds 1' and 2' is not higher than 10:1, and the molar ratio of the compounds 1' and 2' versus compound 3' is not higher than 100:1.

In some embodiments, the catalyst comprises p-toluenesulfonic acid, pyridinium p-toluenesulfonic acid, sulfuric acid, phosphoric acid, nitric acid, hydrogen chloride, molecular sieves, sulfonic acid resin, or solid super acid.

In some embodiments, the first organic solvent comprises tetrahydrofuran or dioxane.

In some embodiments, both X groups together form =O, intermediate compound 4' reacts with hydrazine in a second organic solvent at a temperature in the range of 0-150° C. to produce compound 5'.

In these embodiments, the second organic solvent comprises organic solvent comprises methanol, ethanol, propanol, isopropanol, butanol, isobutanol, t-butanol, pentanol, hexanol, heptanol, octanol, nonanol, decanol, dioxane, tetrahydrofuran, or ethylene glycol; and the hydrazine comprises anhydrous hydrazine or hydrazine hydrate.

Among others, this invention has the following unexpectedly superior advantages:

This invention involves the composite generated by degradable epoxy resin curing agent, epoxy resin, auxiliary material and reinforcing material, which can degrade under relatively mild temperature; more than 95% of reinforcing materials can be recycled (such as carbon fiber, glass fiber, synthetic fiber and natural fiber), can maintain most of the original texture and mechanical properties, and be reused in new composites; the recycled Epoxy resin polymer degradation products can be used in plastic products after processing. The epoxy resin reinforced composite with degradable property, which is generated by degradable epoxy resin curing agent, introduced in this invention has never been reported. The technology has the characteristics of epoxy resin and reinforcing material: high recovery efficiency, simple recycling process and economic.

During the degradation procedure of the said epoxy resin composite, the cross-linked structure of epoxy resin matrix, under the action of acid, will have the specific chemical bonds fracture, and lead to the degradation of epoxy resin matrix; the cross-linked structure transfers to the non-cross-linked epoxy resin polymer (like thermoplastic epoxy resin) which can dissolve in the organic solvent; when the epoxy resin matrix fully dissolves in the organic solvent, fiber reinforcing materials can be separated from the solvent; after Alkali neutralization, sedimentation and solid-liquid separation, recycle the degraded products of epoxy resin matrix from the polymer degradation solvent. Both recycled reinforcing materials and non-cross-linked polymer can be separated, recycled and reused. For now, the reinforcing material of the thermosetting composite can only be recycled after burning out the plastic parts of the composite, however, this invention adopts the biodegradable epoxy resin adhesives composite, the plastic part and reinforcing material of which can be recycled at high efficiency:

(1) Cross-linked epoxy resin curing products, after degradation, can form thermoplastic epoxy resin polymer; small loss of shrinkage group during the degradation process, the recycle quality of thermoplastic epoxy resin polymer is high, and the polymer can be processed for industrial use.

(2) The recycle quality ratio of epoxy resin curing products and reinforcing materials is more than 96%, the recycled reinforcing materials is of very stable quality, clean surface, and no defect under the acid recycle condition.

(3) The recycle methods of degraded epoxy resin composites are characterized by: mild reaction conditions, economic, and easy to control.

As used herein, the term "alkyl," when used alone or as part of a larger moiety (e.g., as in "cycloalkenylalkyl"), refers to a saturated aliphatic hydrocarbon group. It can contain 1 to 12 (e.g., 1 to 8, 1 to 6, or 1 to 4) carbon atoms. As a moiety, it can be denoted as —$C_nH_{2n+1}$. An alkyl group can be straight or branched. Examples of alkyl groups include, but are not limited to, methyl, ethyl, propyl, isopropyl, butyl, isobutyl, sec-butyl, tert-butyl, n-pentyl, n-heptyl, and 2-ethylhexyl. An alkyl group can be substituted (i.e., optionally substituted) with one or more substituents. When an alkyl is preceded by a carbon-number modifier, e.g., $C_{1-8}$, its means the alkyl group contains 1 to 8 carbon atoms.

As used herein, the term "alkylene," when used alone or as part of a larger moiety (e.g., as in "arylaalkyleneoxy"), refers to a saturated aliphatic hydrocarbon group with two radical points for forming two covalent bonds with two other moieties. It can contain 1 to 12 (e.g., 1 to 8, 1 to 6, or 1 to 4) carbon atoms. As a moiety, it can be denoted as —$C_nH_{2n}$—. Examples of an alkylene group include, but are not limited to, methylene (—$CH_2$—), ethylene (—$CH_2CH_2$—), and propylene (—$CH_2CH_2CH_2$—). When an alkylene is preceded by a carbon-number modifier, e.g., $C_{2-8}$, its means the alkylene group contains 2 to 8 carbon atoms.

As used herein, the term "alkynyl," when used alone or as part of a larger moiety (e.g., as in "alkynylalkyl"), refers to an aliphatic hydrocarbon group with at least one triple bond. It can contain 2 to 12 (e.g., 2 to 8, 2 to 6, or 2 to 4) carbon atoms. An alkynyl group can be straight or branched. Examples of an alkynyl group include, but are not limited to, propargyl and butynyl. When an alkynyl is preceded by a carbon-number modifier, e.g., $C_{2-8}$, its means the alkynyl group contains 2 to 8 carbon atoms.

As used herein, the term "alkenyl," when used alone or as part of a larger moiety (e.g., as in "alkenylalkyl""), refers to an aliphatic hydrocarbon group with at least one double bond. It can contain 2 to 12 (e.g., 2 to 8, 2 to 6, or 2 to 4) carbon atoms. An alkenyl group with one double bond can be denoted as —$C_nH_{2n-1}$, or —$C_nH_{2n-3}$ with two double bonds. Like an alkyl group, an alkenyl group can be straight or branched. Examples of an alkenyl group include, but are not limited to, allyl, isoprenyl, 2-butenyl, and 2-hexenyl. When an alkylene is preceded by a carbon-number modifier, e.g., $C_{3-8}$, its means the alkylene group contains 3 to 8 carbon atoms.

As used herein, the term "cycloalkyl," when used alone or as part of a larger moiety (e.g., as in "cycloalkylalkyl"), refers to a saturated carbocyclic mono-, bi-, or tri-cyclic (fused or bridged or spiral) ring system. It can contain 3 to 12 (e.g., 3 to 10, or 5 to 10) carbon atoms. Examples of cycloalkyl groups include, but are not limited to, cyclopropyl, cyclobutyl, cyclopentyl, cyclohexyl, cycloheptyl, adamantyl, norbornyl, cubyl, octahydro-indenyl, decahydro-naphthyl, bicyclo[3.2.1]octyl, bicyclo[2.2.2]octyl, bicyclo[3.3.1]nonyl, bicyclo[3.3.2.]decyl, bicyclo[2.2.2]octyl, adamantyl, azacycloalkyl, or ((aminocarbonyl)cycloalkyl)cycloalkyl. When a cycloalkyl is preceded by a carbon-number modifier, e.g., $C_{3-8}$, its means the alkyl group contains 3 to 8 carbon atoms.

As used herein, the term "cycloalkenyl," when used alone or as part of a larger moiety (e.g., as in "cycloalkenylalkyl"), refers to a non-aromatic carbocyclic ring system having one or more double bonds. It can contain 3 to 12 (e.g., 3 to 10, or 5 to 10) carbon atoms. Examples of cycloalkenyl groups include, but are not limited to, cyclopentenyl, 1,4-cyclohexa-di-enyl, cycloheptenyl, cyclooctenyl, hexahydro-indenyl, octahydro-naphthyl, cyclohexenyl, cyclopentenyl, bicyclo[2.2.2]octenyl, orbicyclo[3.3.1]nonenyl.

As used herein, the term "heterocycloalkyl," when used alone or as part of a larger moiety (e.g., as in "heterocycloalkylalkyl" or "heterocycloalkoxy"), refers to a 3- to 16-membered mono-, bi-, or tri-cyclic (fused or bridged or spiral)) saturated ring structure, in which one or more of the ring atoms is a heteroatom (e.g., N, O, S, or combinations thereof). In addition to the heteroatom(s), the heterocycloalkyl can contain 3 to 15 carbon atoms (e.g., 3 to 12 or 5 to 10). Examples of a heterocycloalkyl group include, but are not limited to, piperidyl, piperazyl, tetrahydropyranyl, tetrahydrofuryl, 1,4-dioxolanyl, 1,4-dithianyl, 1,3-dioxolanyl, oxazolidyl, isoxazolidyl, morpholinyl, thiomorpholyl, octahydrobenzofuryl, octahydrochromenyl, octahydrothiochromenyl, octahydroindolyl, octahydropyrindinyl, decahydroquinolinyl, octahydrobenzo[b]thiopheneyl, 2-oxa-bicyclo[2.2.2]octyl, 1-aza-bicyclo[2.2.2]octyl, 3-aza-bicyclo[3.2.1]octyl, and 2,6-dioxa-tricyclo[3.3.1.03,7]nonyl. A monocyclic heterocycloalkyl group can be fused with a phenyl moiety such as tetrahydroisoquinoline. When a heterocycloalkyl is preceded by a carbon-number modifier, e.g., $C_{4-8}$, its means the heterocycloalkyl group contains 4 to 8 carbon atoms.

As used herein, the term "hetero," when used alone or as part of a larger moiety (e.g., as in "heterocyclo," "heterocycloalkyl," "heterocycloalkylene" or "heteroaryl"), refers to a hetero atom or group that is —O—, —S—, —NH—, or —C(=O)—.

As used herein, the term "aryl," when used alone or as part of a larger moiety (e.g., as in "arylkyl," or "arylkoxy"), refers to a monocyclic (e.g., phenyl), bicyclic (e.g., indenyl, naphthalenyl, or tetrahydronaphthyl), and tricyclic (e.g., fluorenyl, tetrahydrofluorenyl, tetrahydroanthracenyl, or anthracenyl) ring system in which the monocyclic ring system is aromatic (e.g., phenyl) or at least one of the rings in a bicyclic or tricyclic ring system is aromatic (e.g., phenyl). The bicyclic and tricyclic groups include, but are not limited to, benzo-fused 2- or 3-membered carbocyclic rings. For instance, a benzo-fused group includes phenyl fused with two or more $C_{4-8}$ carbocyclic moieties.

As used herein, the term "heteroaryl" refers to a monocyclic, bicyclic, or tricyclic ring system having 5 to 15 ring atoms wherein at least one of the ring atoms is a heteroatom (e.g., N, O, S, or combinations thereof) and when the monocyclic ring system is aromatic or at least one of the rings in the bicyclic or tricyclic ring systems is aromatic. It can contain 5 to 12 or 8 to 10 ring atoms. A heteroaryl group includes, but is not limited to, a benzo-fused ring system having 2 to 3 rings. For example, a benzo-fused group includes benzo fused with one or two 4- to 8-membered heterocycloalkyl moieties (e.g., indolizyl, indolyl, isoindolyl, 3H-indolyl, indolinyl, benzo[b]furyl, benzo[b]thiophenyl, quinolinyl, or isoquinolinyl). Some examples of heteroaryl are pyridyl, IH-indazolyl, furyl, pyrrolyl, thienyl, thiazolyl, oxazolyl, imidazolyl, tetrazolyl, benzofuryl, isoquinolinyl, benzithiazolyl, xanthenyl, thioxanthenyl, phenothiazinyl, dihydroindolyl, benzo[1,3]dioxolyl, benzo[b]furyl, benzo[b]thiophenyl, indazolyl, benzimidazolyl, benzthiazolyl, puryl, quinolinyl, quinazolinyl, phthalazyl, quinazolyl, quinoxalyl, isoquinolinyl, 4H-quinolizyl, benzo-1,2,5-thiadiazolyl, and 1,8-naphthyridyl.

As used herein, the term "alkoxyalkyl" refers to alkyl-O-alkyl, and example of which is $C_2H_5$—O—$C_2H_4$—.

As used herein, the suffix "-ene" is used to describe a bivalent group with two radical points for forming two covalent bonds with two other moieties. In other words, any of the terms as defined above can be modified with the suffix "-ene" to describe a bivalent version of that moiety. For example, a bivalent aryl ring structure is "arylene," a bivalent benzene ring structure is "phenylene," a bivalent heteroaryl ring structure is "heteroarylene," a bivalent cycloalkyl ring structure is a "cycloalkylene," a bivalent heterocycloalkyl ring structure is "heterocycloalkylene," a bivalent cycloalkenyl ring structure is "cycloalkenylene," a bivalent alkenyl chain is "alkenylene," and a bivalent alkynyl chain is "alkynylene."

As used herein, the term "optionally" (e.g., as in "optionally substituted with") means that the moiety at issue is either substituted or not substituted, and that the substitution occurs only when chemically feasible. For instance, H cannot be substituted with a substituent and a covalent bond or —C(═O)— group cannot be substituted with a substituent.

As used herein, an "oxo" group refers to ═O.

As used herein, a "carbonyl" group refers to —C(O)— or —C(═O)—.

As used herein, the term "substituted," whether preceded by the term "optionally" or not, refers to the replacement of hydrogen radicals in a given structure with the radical of a specified substituent. Specific substituents are described above in the definitions and below in the description of compounds and examples thereof. Unless otherwise indicated, an optionally substituted group can have a substituent at each substitutable position of the group, and when more than one position in any given structure can be substituted with more than one substituent selected from a specified group, the substituent can be either the same or different in every position. A ring substituent, such as a heterocycloalkyl, can be bound to another ring, such as a cycloalkyl, to form a spiro-bicyclic ring system, e.g., both rings share one common atom. As one of ordinary skill in the art will recognize, combinations of substituents envisioned by this invention are those combinations that result in the formation of stable or chemically feasible compounds.

For convenience and as commonly understood, the term "optionally substituted" only applies to the chemical entities that can be substituted with suitable substituents, not to those that cannot be substituted chemically.

As used herein, the term "or" can mean "or" or "and."

DETAILED DESCRIPTION OF THE INVENTION

The following examples are provided for illustration only, and not intended to be limiting in any aspect.

Example 1: Preparation of Curing Agent 1

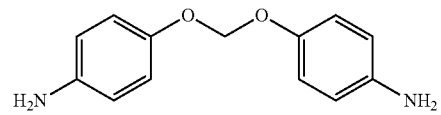

Method 1:

100 g potassium p-nitrophenolate and 98.3 g dibromomethane were placed in 400 ml N, N-dimethylformamide (DMF) in a 1 L three-neck round bottom flask, the solution was heated to react at 120° C. for 18 hours, DMF was recycled at reduced pressure, after the residue was cooled, water was added till yellow precipitate was appeared, filtered, the solid was dried at vacuum to give 70 g bis(4-nitrophenoxy)methane.

Intermediate bis(4-nitrophenoxy)methane was placed in 1.5 L tetrahydrofuran in 2 L three-neck round bottom flask, 7 g 10% Pd/C and 140 g 80% hydrazine hydrate were added, the reaction was heated to reflux, after 5 hours at reflux, cooled, filtered and 10% Pd/C was recycled, the mother liquid was evaporated by rotary evaporator, the residue was recrystallized with petroleum ether/ethyl acetate to give 50 g Curing Agent 1 (i.e., 4,4'-(methylenebis(oxy))dianiline), the total yield of the two steps was 77%.

Method 2:

400 g DMF, 200 g sodium p-nitrophenolate, and 121.6 g dichloromethane were mixed and placed in a 1 L flask, the solution was heated to reflux. After 3 hours (the reaction was completed by TLC monitoring) the solution was cooled, filtered, the filtrate was concentrated at reduced pressure. The residue was cooled, water was added till white precipitate was appeared, filtered, the solid was dried at vacuum to give 170 g bis(4-nitrophenoxy)methane, the yield was about 94%.

170 g bis(4-nitrophenoxy)methane, 680 g ethanol, 21.5 g ferric chloride and 76.5 g activated carbon were placed in a 2 L flask, the reaction was heated to reflux, after at least 30 minutes, hydrazine hydrate was dripped in at reflux, the drip off was controlled within 3 hours. The reaction was preserved the temperature to reflux (after 4 hours the reaction was completed by TLC monitoring), filtered when the solution was hot. The filter residue was washed with small amount of ethanol, the filtrate was cooled, and the precipitate was appeared, filtered, the solid was dried at vacuum to give 120 g Curing Agent 1 (i.e., 4,4'-(methylenebis(oxy)) dianiline), the total yield of the two steps was 89%.

mp=104-107° C.

1H-NMR (CDCl3, 400 MHz): 6.94 (d, 4H), 6.65 (d, 4H), 5.52 (s, 2H), 3.40 (br, 4H).

Example 2: Preparation of Curing Agent 2

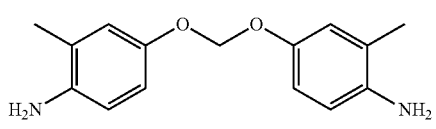

2

100 g 3-methyl-4-nitrophenol and 40 g potassium hydroxide were placed in 2.5 L ethanol in a 5 L three-neck round bottom flask, after 5 hours at room temperature, the solution was evaporated by rotary evaporator to give 120 g potassium 3-methyl-4-nitrophenolate.

56 g dibromomethane and the solid were dissolved in 500 mL DMF, the reaction was heated to 120° C., after 5 hours, DMF was recycled at reduced pressure, after the residue was cooled, water was added till yellow precipitate was appeared, filtered and collected, the solid was dried at vacuum to give 80 g dimethane (bis(3-methyl-4-nitrophenoxy)methane).

80 g bis(3-methyl-4-nitrophenoxy)methane, 1.5 L dioxane and 4 g Raney-Ni were placed in a 2 L three-neck round bottom flask, the reaction was heated to reflux, 140 g 80% hydrazine hydrate were dripped in the reaction, after 10 hours, filtered and Raney-Ni was recycled, the mother liquid was concentrated, the residue was recrystallized with petroleum ether/ethyl acetate to give 50 g Curing Agent 2 (i.e., 4,4'-(methylenebis(oxy))bis(2-methylaniline)), the yield was 69.5%.

mp=75-80° C.

1H-NMR (CDCl3, 400 MHz): 6.84 (s, 2H), 6.80 (d, 2H), 6.60 (d, 2H), 5.50 (s, 2H), 3.40 (br, 4H), 2.13 (s, 6H).

Example 3: Preparation of Curing Agent 3

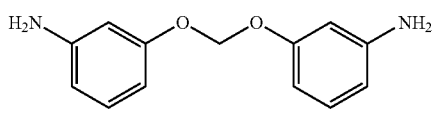

3

100 g potassium m-nitrophenolate and 98.3 g dibromomethane were placed in 400 mL N,N-dimethylformamide (DMF) in a 1 L three-neck round bottom flask, the solution was heated to react at 125° C. for 10 hours, DMF was recycled at reduced pressure, after the residue was cooled, water was added till yellow precipitate was appeared, filtered, the solid was dried at vacuum to give 70 g bis (3-nitrophenoxy) methane.

The intermediate was placed in 1.5 L dioxane in a 2 L three-neck round bottom flask, 7 g Raney-Ni was added, the reaction was heated to reflux, 140 g 80% hydrazine hydrate were dripped in the reaction, the reaction was completed by TLC monitoring. The solution was filtered, and Raney-Ni was recycled, the mother liquid was concentrated under reduced pressure, the residue was recrystallized with petroleum ether/ethyl acetate to give 50 g curing agent 3 (i.e., 3,3'-(methylenebis(oxy))dianiline), the total yield of the two steps was 77%.

mp: 121-124° C.

1H-NMR (CDCl3, 400 MHz): 7.06 (t, 2H), 6.50 (d, 2H), 6.44 (s, 2H), 6.36 (d, 2H), 5.64 (s, 2H), 3.67 (br, 4H).

Example 4: Preparation of Curing Agent 4

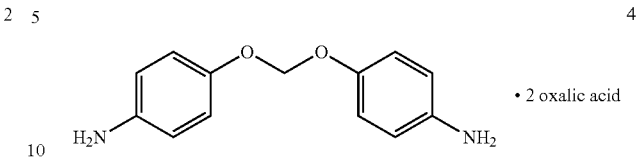

4

· 2 oxalic acid 420 g 4,4'-(methylenebis(oxy))dianiline, 460 g oxalic acid and 2100 g ethanol were mixed at room temperature, the reaction was heated to reflux for 3 hours, cooled to room temperature, filtered, the solid was washed with ethanol, dried to give 580 g Curing Agent 4.

Example 5: Preparation of Curing Agent 5

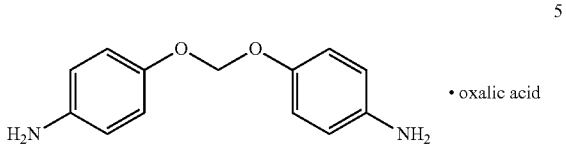 [SMILES: Nc1ccc(OCOc2ccc(N)cc2)cc1]

5

· oxalic acid 420 g 4,4'-(methylenebis(oxy))dianiline, 230 g oxalic acid and 1600 g ethanol were mixed at room temperature, the reaction was heated to reflux for 3 hours, cooled to room temperature, filtered, the solid was washed with ethanol, dried to give 520 g Curing Agent 5.

Example 6: Preparation of Curing Agent 6

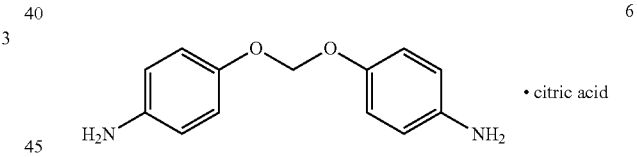

6

· citric acid 420 g 4,4'-(methylenebis(oxy))dianiline, 274 g citric acid and 1200 g ethanol were mixed at room temperature, the reaction was heated to reflux for 3 hours, cooled to room temperature, filtered, the solid was washed with ethanol, dried to give 510 g Curing Agent 6.

Example 7: Preparation of Curing Agent 7

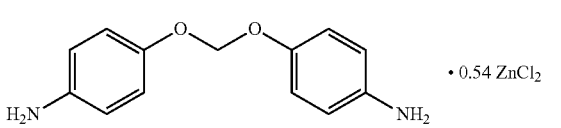

7

· 0.54 ZnCl2

50 g 4,4'-(methylenebis(oxy))dianiline, 16 g zinc chloride and 200 g ethanol were mixed at room temperature, the reaction was heated to reflux for 4 hours, cooled to room temperature, filtered, the solid was washed with ethanol, dried to give 54 g curing agent 7.

Example 8: Degradable Cross-Linked Polymer Polymerized by the Curing Agent and Epoxy Resin 76.5 g curing agent 1 from Example 1 (AEW≈1.74 N—H eq./100 g) and 250 g liquid bisphenol A epoxy resin 828 (EEW 0.52~0.54 eq./100 g) were mechanically mixed and stirred evenly at room temperature, the viscosity of the mixture was tested at 65° C., the viscosity was 1100-2000 cps (SNB-1Digital Display Viscosity Meter), gel time was 210 minutes, the viscosity and gel time of the mixture after 7 days preserved at −20° C. and 28 days preserved at 65° C. were tested separately.

Example 9-12: Degradable Cross-Linked Polymer Polymerized by the Curing Agent and Epoxy Resin Curing agent 1 from Example 1 (AEW≈1.74 N—H eq./100 g), liquid bisphenol A epoxy resin 828 (EEW 0.52~0.54 eq./100 g) and solid bisphenol A epoxy resin E20 (EEW=0.18~0.22 eq./100 g) were mechanically mixed and stirred evenly at room temperature with different ratios. The viscosity and gel time of the mixture was tested at 65° C. (SNB-1Digital Display Viscosity Meter), the viscosity and gel time of the mixture after 7 days preserved at −20° C. and 28 days preserved at 65° C. were tested separately, the results were as in the following table 1.

TABLE 1

| | amounts of epoxy resin | | amounts of | viscosity (cps) 65° C. | | | Gel time (minute) | | |
|---|---|---|---|---|---|---|---|---|---|
| Example | 28 | 20 | curing agent I | 0 day | 7 days | 28 days | 0 day | 7 days | 28 days |
| 8 | 50 | | 76.5 | 1100-2000 | 1000-1500 | 1000-1700 | 210 | 190 | 160 |
| 9 | 00 | 0 | 67.0 | 2500-2900 | 1800-2300 | 2500-3500 | 150 | 120 | 120 |
| 10 | 50 | 00 | 57.4 | 7000-10000 | 6000-12000 | 9000-12000 | 60 | 60 | 65 |
| 11 | 00 | 50 | 47.8 | 8000-12000 | 8500-13000 | 20000-25000 | 45 | 45 | 45 |
| 12 | 0 | 00 | 38.3 | 11000-17000 | n/a | n/a | 28 | 27 | 25 |

Each 10 g mixture of the samples in Example 8-12 was separately placed on the glass slide, the reaction was heated in the oven at 125° C., after 3 hours completely cured, the cured sample of epoxy resin was prepared, the glass-transition temperature (Tg) was tested with DSC, the results were as in the 2.

TABLE 2

| Example | Tg (° C.) |
|---|---|
| 8 | 133~134 |
| 9 | 134~136 |
| 10 | 131~135 |
| 11 | 130~132 |
| 12 | 119~120 |

Example 13: Degradable Cross-Linked Polymer Polymerized by the Curing Agent and Epoxy Resin 64.4 g curing agent II in Example 2 (AEW≈1.55 N—H eq./100 g), 120 g liquid bisphenol A epoxy resin 828 (EEW 0.52~0.54 eq./100 g) and 180 g solid bisphenol A epoxy resin E20 (EEW=0.18~0.22 eq./100 g) were mechanically mixed and stirred evenly at room temperature, the viscosity of the mixture was tested at 65° C., the viscosity was 16000-19000 cps (SNB-1Digital Display Viscosity Meter), gel time was 80 minutes, the viscosity and gel time of the mixture after 7 days preserved at −20° C. and 28 days preserved at 65° C. were tested separately, the results were in table 3.

10 g mixture sample was placed on the glass slide, the reaction was heated in the oven at 125° C., after 3 hours completely cured, the Tg of the cured sample was 80-85° C. (table 4).

Example 14: Degradable Cross-Linked Polymer Polymerized by the Curing Agent and Epoxy Resin 57.3 g curing agent iii in Example 3 (AEW~1.74 N—H eq./100 g), 120 g liquid bisphenol A epoxy resin 828 (EEW 0.52~0.54 eq./100 g) and 180 g solid bisphenol A epoxy resin E20 (EEW=0.18~0.22 eq./100 g) were mechanically mixed and stirred evenly at room temperature, the viscosity of the mixture was tested at 65° C., the viscosity was 16000-19000 cps (SNB-1Digital Display Viscosity Meter), gel time was 80 minutes, the viscosity and gel time of the mixture after 7 days preserved at −20° C. and 28 days preserved at 65° C. were tested separately, the results were in table 3.

10 g mixture sample was placed on the glass slide, the reaction was heated in the oven at 125° C., after 3 hours completely cured, the Tg of the cured sample was 86-89° C. (table 4).

Comparative Example C1

49.5 g 4,4'-Methylenedianiline (DDM, AEW≈2.02 N—H eq./100 g), 120 g liquid bisphenol A epoxy resin 828 (EEW 0.52~0.54 eq./100 g) and 180 g solid bisphenol A epoxy resin E20 (EEW=0.18~0.22 eq./100 g) were mechanically mixed and stirred evenly at room temperature, the viscosity of the mixture was tested at 65° C., the viscosity was 8000-10000 cps (SNB-1Digital Display Viscosity Meter), gel time was 30 minutes, the viscosity and gel time of the mixture after 7 days preserved at −20° C. and 28 days preserved at 65° C. were tested separately, the results were in table 3.

10 g mixture sample was placed on the glass slide, the reaction was heated in the oven at 125° C., after 3 hours completely cured, the Tg of the cured sample was 137-139° C. (see table 4).

Comparative Example C2

21 g dicyandiamide, 120 g liquid bisphenol A epoxy resin 828 (EEW 0.52~0.54 eq./100 g) and 180 g solid bisphenol A epoxy resin E20 (EEW=0.18~0.22 eq./100 g) were mechanically mixed and stirred evenly at room temperature, the viscosity of the mixture was tested at 65° C., the viscosity was 13600-15400 cps (SNB-1Digital Display Viscosity Meter), no gel was formed after 24 hours, the viscosity and gel time of the mixture after 7 days preserved at −20° C. and 28 days preserved at 65° C. were tested separately, the results were in table 3.

TABLE 3

| Example | amounts of epoxy resin 828 | E20 | amounts of curing agent | | Viscosity (Cps) 65° C. 0 day | 7 days | 28 days | Gel time (Minute) 0 day | 7 days | 28 days |
|---|---|---|---|---|---|---|---|---|---|---|
| 11 | 100 | 150 | Curing agent i | 47.8 | 8000-12000 | 8500-13000 | 20000-25000 | 45 | 45 | 45 |
| 13 | 120 | 180 | Curing agent ii | 64.4 | 16000-19000 | 17000-19000 | 20000-25000 | 80 | 80 | 80 |
| 14 | 120 | 180 | Curing agent iii | 57.3 | 23000-25000 | 23000-25000 | 15000-25000 | 180 | 180 | 170 |
| C1 | 120 | 180 | DDM | 49.5 | 8000-10000 | 15000-25000 | 20000-30000 | 30 | 30 | 30 |
| C2 | 120 | 180 | DICY | 21.0 | 13600-15400 | 13500-16000 | 12000-16000 | >24 h | >24 h | >24 h |

TABLE 4

| Example | Tg (° C.) |
|---|---|
| 11 | 130~132 |
| 13 | 80~85 |
| 14 | 86~89 |
| C1 | 137~139 |

Example 15: Degradation of Degradable Cross-Linked Polymer 10 g cured samples in example 11, 10 mL concentrated hydrochloric acid and 90 mL ethylene glycol were placed in a 250 mL three-neck flask, stirred and heated to 155° C., completely degraded after 4 hour, the solution was neutralized with 10% sodium hydroxide solution and precipitated solid was filtered and the solid was washed with water and dried to give 9.6 g of degradation products of epoxy resin, mass recovery ratio was 96%.

The molecular weight of the degradation products of epoxy resin was analyzed with GPC, Mn=25403 Da, Mw=37676 Da, PDI=1.48

Example 16: Degradation of Degradable Cross-Linked Polymer 10 g cured samples in example 13, 10 ml concentrated hydrochloric acid and 90 mL ethylene glycol were placed in a 250 ml three-neck flask, stirred and heated to 190° C., completely degraded after 4 hour, the solution was neutralized with 90% sodium hydroxide solution and precipitated solid was filtered and the solid was washed with water and dried to give 9.78 g of degradation products of epoxy resin, mass recovery ratio was 98%.

Example 17: Degradation of Degradable Cross-Linked Polymer 10 g cured samples in example 14, 10 ml concentrated hydrochloric acid and 90 mL ethylene glycol were placed in a 250 ml three-neck flask, stirred and heated to 155° C., completely degraded after 4 hour, and brown transparent solution was obtained, the solution was neutralized with 0.1% sodium hydroxide solution and precipitated solid was filtered and the solid was washed with water and dried to give 9.8 g of degradation products of epoxy resin, mass recovery ratio was 98%.

Comparative Example C3

10 g cured samples in comparative example C1, 10 ml concentrated hydrochloric acid and 90 mL ethylene glycol were placed in a 250 ml three-neck flask, stirred and heated to 155° C., the cured product was not degraded after 4 hours.

Example 18: Degradable Cross-Linked Polymer Polymerized by the Curing Agent and Epoxy Resin 5 g solid bisphenol A epoxy resin E20 (EEW=0.18~0.22 eq./100 g) and 3.5 g novolac epoxy resin F51 (EEW 0.51~0.54 eq./100 g) were mixed and stirred evenly at 100° C., cooled to 70° C., 1.5 g bisphenol A epoxy resin E44 (EEW=0.41~0.47 eq./100 g) and 3.5 g curing agent iv (AEW≈0.98 N—H eq./100 g) in example 4 were added, mixed and stirred evenly, gel time at 70° C. was more than 5 hours.

10 g of the mixture sample was placed on the glass slide; the reaction was heated in the oven at 150° C. for 2 hours.

Example 19: Degradable Cross-Linked Polymer Polymerized by the Curing Agent and Epoxy Resin 5 g solid bisphenol A epoxy resin E20 (EEW=0.18~0.22 eq./100 g) and 3.5 g novolac epoxy resin F51 (EEW 0.51~0.54 eq./100 g) were mixed and stirred evenly at 100° C., cooled to 70° C., 1.5 g liquid bisphenol A epoxy resin 828 (EEW=0.52~0.54 eq./100 g) and 3.6 g curing agent iv (AEW≈0.98 N—H eq./100 g) in example 4 were added, mixed and stirred evenly, gel time at 70° C. was more than 5 hours.

10 g of the mixture sample was placed on the glass slide; the reaction was heated in the oven at 150° C. for 2 hours.

Example 20: Degradation of Degradable Cross-Linked Polymer 10 g cured samples in example 18, 10 mL concentrated hydrochloric acid and 90 mL ethylene glycol were placed in a 250 mL three-neck flask, stirred and heated to 155° C., completely degraded after 4 hour, and brown transparent solution was obtained, the solution was neutralized with 70% sodium hydroxide solution and precipitated solid was filtered and the solid was washed with water and dried to give 9.82 g of degradation products of epoxy resin, mass recovery ratio was 98%.

Example 21: Degradation of Degradable Cross-Linked Polymer 10 g cured samples in example 19, 10 mL concentrated hydrochloric acid and 90 mL ethylene glycol were placed in a 250 ml three-neck flask, stirred and heated to 155° C., completely degraded after 4 hour, and brown transparent solution was obtained, the solution was neutralized with 5% sodium hydroxide solution and precipitated solid was filtered and the solid was washed with water and dried to give 9.79 g of degradation products of epoxy resin, mass recovery ratio was 98%.

Example 22: Degradable Cross-Linked Polymer Polymerized by the Curing Agent and Epoxy Resin 5 g solid bisphenol A epoxy resin E20 (EEW=0.18~0.22 eq./100 g) and 3.5 g novolac epoxy resin F51 (EEW 0.51~0.54 eq./100 g) were mixed and stirred evenly at 100° C., cooled to 70° C., 1.5 g bisphenol A epoxy resin E44 (EEW=0.41~0.47 eq./100 g) and 2.73 g curing agent v (AEW≈1.25 N—H eq./100 g) in example 4 were added, mixed and stirred evenly, gel time at 70° C. was more than 5 hours.

10 g of the mixture sample was placed on the glass slide; the reaction was heated in the oven at 150° C. for 2 hours.

Example 23: Degradation of Degradable Cross-Linked Polymer 10 g cured samples in example 22, 10 ml concentrated hydrochloric acid and 90 mL ethylene glycol were placed in a 250 ml three-neck flask, stirred and heated to 150° C., completely degraded after 4 hour, and brown transparent solution was obtained, the solution was neutralized with 90% sodium hydroxide solution and precipitated solid was filtered and the solid was washed with water and dried to give 9.83 g of degradation products of epoxy resin, mass recovery ratio was 98%.

Example 24: Degradable Cross-Linked Polymer Polymerized by the Curing Agent and Epoxy Resin 5 g solid bisphenol A epoxy resin E20 (EEW=0.18~0.22 eq./100 g) and 3.5 g novolac epoxy resin F51 (EEW 0.51~0.54 eq./100 g) were mixed and stirred evenly at 100° C., cooled to 70° C., 1.5 g bisphenol A epoxy resin E44 (EEW=0.41~0.47 eq./100 g) and 3.6 g curing agent vi (AEW≈0.95 N—H eq./100 g) in example 6 were added, mixed and stirred evenly, gel time at 70° C. was more than 5 hours.

10 g of the mixture sample was placed on the glass slide; the reaction was heated in the oven at 150° C. for 2 hours.

Example 25: Degradation of Degradable Cross-Linked Polymer 10 g cured samples in example 24, 10 mL concentrated hydrochloric acid and 90 mL ethylene glycol were placed in a 250 mL three-neck flask, stirred and heated to 150° C., completely degraded after 4 hour, and brown transparent solution was obtained, the solution was neutralized with 10% sodium hydroxide solution and precipitated solid was filtered and the solid was washed with water and dried to give 9.8 g of degradation products of epoxy resin, mass recovery ratio was 98%.

Example 26: Preparation of Degradable Epoxy Matrix 15 g bisphenol A epoxy resin E51 (EEW 0.48-0.54 eq./100 g) and 36 g curing agent 6 (AEW≈0.95 N—H eq./100 g) in example 6 were weighed and mixed in a blender, then grinded in a three-roll mill for 30 minutes, as standby. 20 g bisphenol A epoxy resin E51 (EEW 0.48-0.54 eq./100 g), 15 g E44 (EEW 0.41-0.47 eq./100 g) and 50 g E20 (EEW 0.18-0.22 eq./100 g) were placed in an oven preheated to 120° C. for 3 hours, then put into a kneader to knead for 1 hour, cooled to 70° C., then the resin was put into mixing blender, then vacurated at 70° C., former standby E51/curing agent vi mixture system was stirred at high speed for 30 minutes, discharged, and cooled to room temperature, then frozen in store.

Above prepared degradable epoxy matrix, the gel time was more than 4 hours at 70° C., can be preserved more than a month at room temperature, can be preserved more than half a year at 0° C., can be preserved more than a year at −18° C.

Preparation of degradable epoxy carbon fiber prepreg and carbon fiber composite laminate: The above prepared epoxy system was heated to 70° C., and carbon fiber prepreg was made using 3K carbon cloth by wet method, the prepregs were slightly tacky at room temperature, and pressed on the tablet pressing machine at 150° C. to give laminate of carbon fiber composite.

Example 27: Degradation of the Reinforced Composite 1 g sample of the carbon fiber composite laminate in example 26, 10 mL concentrated hydrochloric acid and 90 mL phenylcarbinol were placed in a one-neck round bottom flask, stirred and heated to 140° C., after 4 hours filtered when the solution was hot, the carbon fiber and the degradation solution were separated, the solution was neutralized with 30% sodium hydroxide solution and precipitated solid was filtered and the solid was washed with water and dried to give 0.98 g degradation products of thermoset epoxy resin and carbon fiber, mass recovery ratio was 98%. The surface of recycled fiber was clean and basically no defect

Example 28: Degradation of the Reinforced Composite 1 g sample of the carbon fiber composite laminate in example 26, 0.1 mL concentrated hydrochloric acid and 90 mL phenylcarbinol were placed in an autoclave, stirred and heated to 350° C., epoxy resin matrix was completely degraded after 1 hour, cool down to 100° C., filtered when the solution was hot, the carbon fiber and the degradation solution were separated, the solution was neutralized with 0.1% sodium hydroxide solution and precipitated solid was filtered and the solid was washed with water and dried to give 0.95 g degradation products of thermoset epoxy resin and carbon fiber, mass recovery ratio was 95%

Example 29: Degradation of the Reinforced Composite 0.1 g sample of the carbon fiber composite laminate in example 26, 90 mL concentrated hydrochloric acid and 2 mL phenylcarbinol were placed in a one-neck round bottom flask, stirred and heated to 20° C., completely degraded after 120 hours, filtered, the carbon fiber and the degradation solution were separated, the solution was neutralized with 100% sodium hydroxide solution and precipitated solid was filtered and the solid was washed with water and dried to give 0.096 g degradation products of thermoset epoxy resin and carbon fiber, mass recovery ratio was 96%.

Example 30: Degradable Cross-Linked Polymer Polymerized by the Curing Agent and Epoxy Resin 5 g solid bisphenol A epoxy resin E20 (EEW=0.18~0.22 eq./100 g) and 3.5 g novolac epoxy resin F51 (EEW 0.51~0.54 eq./100 g) were mixed and stirred evenly at 100° C., cooled to 70° C., 1.5 g liquid bisphenol A epoxy resin 828 (EEW=0.52~0.54 eq./100 g) and 2.7 g curing agent vii (AEW≈1.32 N—H eq./100 g) in example 7 were added, mixed and stirred evenly, gel time at 70° C. was more than 4 hours.

10 g of the mixture sample was placed on the glass slide; the reaction was heated in the oven at 150° C. for 2 hours.

Example 31: Degradation of Degradable Cross-Linked Polymer 10 g cured samples in example 30, 10 mL concentrated hydrochloric acid and 90 mL ethylene glycol were placed in a 250 mL three-neck flask, stirred and heated to 155° C., completely degraded after 4 hour, and brown transparent solution was obtained, the solution was neutralized with 70% sodium hydroxide solution and precipitated solid was filtered and the solid was washed with water and dried to give 9.82 g of degradation products of epoxy resin, mass recovery ratio was 98%.

Example 32: Preparation of Curing Agent 32

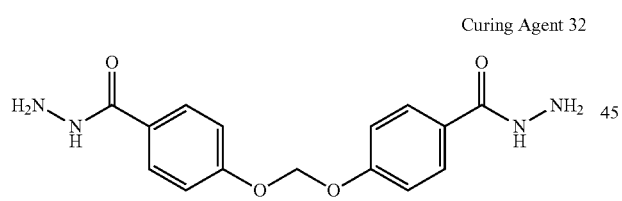

Curing Agent 32

10 g Methylparaben, 6.8 g dibromomethane and 3.9 g sodium hydroxide were placed in 25 mL of N, N-dimethylformamide (DMF) in a 250 mL three-neck round bottom flask equipped with a condenser. The solution was heated to reflux. After 5 hours at reflux, the reaction was cooled to room temperature, then mother liquid was concentrated, water was added and precipitate was obtained, filtered, dried to afford 3 g of solid intermediate.

The solid intermediate was dissolved in 10 mL ethanol in a 250 mL three-neck round bottom flask equipped with a condenser, then 1.4 g hydrazine hydrate was added, the reaction was heated to 78° C. under reflux for 2 hours, then cooled to below 5° C. The solid was precipitated, filtered and washed with ethanol to give 1.5 g white solid product.

Melting point: 248-249° C.

1H-NMR (400 MHz, d6-DMSO): 9.66 (s, 2H), 7.81 (d, 4H), 7.14 (d, 4H), 5.96 (s, 2H), 4.45 (s, 4H).

LC/MS (M H): 317.

Example 33: Preparation of Curing Agent 33

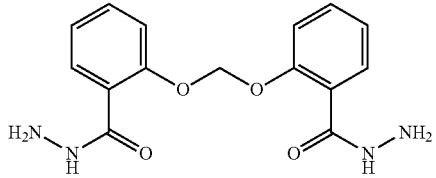

Curing Agent 33

10 g 2-(methoxycarbonyl) phenol, 6.8 g dibromomethane and 3.9 g sodium hydroxide were dissolved in 25 mL of DMF in a 250 mL three-neck round bottom flask equipped with a condenser. The solution was heated to reflux. After 5 hours at reflux, the reaction was cooled to room temperature, then mother liquid was concentrated, water was added and precipitate was obtained, filtered, dried to afford 3 g of solid intermediate.

The solid intermediate was dissolved in 10 mL ethanol in a 250 mL three-neck round bottom flask equipped with a condenser, then 1.4 g hydrazine hydrate was added, the reaction was heated to 78° C. under reflux for 2 hours, then cooled to below 5° C. The solid was precipitated, filtered and washed with ethanol to give 1.1 g white solid product.

Melting point: 174-180° C.

1H-NMR (400 MHz, d6-DMSO): 9.32 (s, 2H), 7.59 (d, 2H), 7.46 (t, 2H), 7.39 (d, 2H), 7.12 (t, 2H), 5.95 (s, 2H), 4.49 (br, 4H).

LC/MS (M H): 317.

Example 34: Preparation of Curing Agent 34

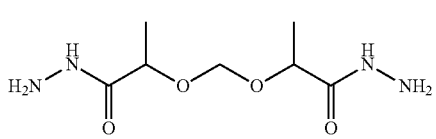

Curing Agent 34

300 g toluene, 150 g ethyl lactate, 20 g paraformaldehyde and 2.2 g p-toluenesulfonic acid were placed in a 250 mL three-neck round bottom flask equipped with a condenser. The reaction was heated to reflux for 7 hours and the evolved water was removed. Then the reaction solution was washed with 100 mL of saturated brine for 8 times, the organic phase was concentrated, then the preceding fraction (less than 60° C.) was distilled out of the residue under reduced pressure and the remaining residue was 90 g.

The remaining residue was dissolved with ethanol, and then 86 g 85% hydrazine hydrate was added. The reaction was heated to reflux for 4 hours, and then cooled, and the solution was concentrated under reduced pressure to give an oil, then freezed, crystal was precipitated, filtered and washed with ethanol until filtrate was colorless, then dried to give 15 g white solid.

Melting point: 138-139° C.

1H-NMR (400 MHz, d6-DMSO): 9.1 (s, 2H), 4.58 (s, 2H), 4.23 (s, 4H), 4.09 (m, 2H), 1.23 (d, 6H).

LC/MS (M+H$^+$): 221.

Example 35: Preparation of Curing Agent 35

Curing Agent 35

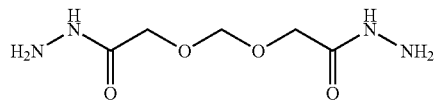

300 g toluene, 24 g Ethyl glycolate, 14 g paraformaldehyde, and 0.43 g p-toluenesulfonic acid were placed into the 500 mL three-neck round bottom flask equipped with a condenser. The reaction was heated to reflux for 7 hours and the evolved water was removed. The reaction solution was washed with 250 mL of saturated brine for 8 times, then the organic phase was concentrated, then the preceding fraction (less than 60° C.) was distilled out of the residue under reduced pressure. The remaining residue was dissolved in ethanol and 20 g 85% hydrazine hydrate was added. The reaction was heated to reflux for 4 hours, and then cooled, and the solution was concentrated under reduced pressure to give oil, then freezed, crystal was precipitated, filtered and washed with ethanol until filtrate was colorless, then dried to give 3.1 g white solid.

Melting point: 115-116° C.

1H-NMR (400 MHz, DMSO): 9.07 (s, 2H), 4.66 (s, 2H), 4.25 (s, 4H), 3.97 (s, 4H).

LC/MS (M+H$^+$): 193.

Example 36: Degradable Cross-Linked Polymer Polymerized by Curing Agent and Epoxy Resin At room temperature, 10 grams of curing agent 32 in Example 32 (AEW≈1.26 NH eq./100 g) and 23.8 g liquid bisphenol A epoxy resin E52D (EEW 0.52~0.54 eq./100 g) were mixed and stirred evenly, under 70° C. conditions, the gel time of the resin mixture was more than 4 hours, shelf time of the resin mixture was more than a month at room temperature. Appropriate amount of the resin mixture was painted on a glass slide, heated to 120° C. for 2 hours, and then 160° C. for 2 hours until fully cured to give the sample of cured degradable epoxy resin.

Example 37: Degradable Cross-Linked Polymer Polymerized by Curing Agent and Epoxy Resin At room temperature, 10 grams of curing agent II in Example 2 (AEW≈1.26 NH eq./100 g) and 23.8 g liquid bisphenol A epoxy resin E52D (EEW 0.52~0.54 eq./100 g) were mixed and stirred evenly, under 70° C. conditions, the gel time of resin mixture was more than 4 hours, shelf time of the resin mixture was more than a month at room temperature. Appropriate amount of the resin mixture was painted on a glass slide, heated to 120° C. for 2 hours, and then 160° C. for 2 hours until fully cured to give the sample of cured degradable epoxy resin.

Example 38: Degradable Cross-Linked Polymer Polymerized by Curing Agent and Epoxy Resin At room temperature, 10 grams of curing agent 34 in Example 34 (AEW≈1.81 NH eq./100 g) and 32 g liquid bisphenol F epoxy resin E52D (EEW 0.5~0.63 eq./100 g) mixed and stirred evenly, under 70° C. conditions, the gel time of resin mixture was more than 4 hours, half time of the resin mixture was more than a month at room temperature. Appropriate amount of the resin mixture was painted on a glass slide, heated to 70° C. for 2 hours, and then 125° C. for 2 hours until fully cured to give the sample of cured degradable epoxy resin.

Example 39: Degradable Cross-Linked Polymer Polymerized by Curing Agent and Epoxy Resin At room temperature, 10 grams of curing agent 35 in Example 35 (AEW≈2.07 N—H eq./100 g) and 36.6 g liquid bisphenol F epoxy resin E52D (EEW0.5~0.63 eq./100 g) were mixed and stirred evenly, under 70° C. conditions, the gel time of the resin mixture more than 4 hours, shelf time of the resin mixture was more than a month at room temperature. Appropriate amount of the resin mixture was painted on a glass slide, heated to 70° C. for 2 hours, then 125° C. heating for 2 hours until fully cured and be prepared to the sample of cured degradable epoxy resin.

Example 40: Degradation of Degradable Cross-Linked Polymer 0.5 g of the samples of cured sample in Example 5, 10 mL concentrated hydrochloric acid and 90 mL ethylene glycol were placed in a one-neck round flask, stirred and heated to 180° C., completely degraded after 10 hours and transparent clear solution was obtained, which was neutralized with 20% sodium hydroxide solution and precipitated solid was filtered and the solid was washed with water and dried to give 0.48 g of degradation products of thermoset epoxy resin, mass recovery ratio was 95%.

Example 41: Degradation of Degradable Cross-Linked Polymer 0.48 g of the samples of cured sample in Example 37, 0.1 mL concentrated hydrochloric acid and 90 mL ethylene glycol were placed in an autoclave, stirred and heated to 350° C., completely degraded after 0.5 hours and transparent clear solution was obtained, which was neutralized with 20% sodium hydroxide solution and precipitated solid was filtered and the solid was washed with water and dried to give 0.46 g of degradation products of thermoset epoxy resin, mass recovery ratio was 95%.

Example 42: Degradation of Degradable Cross-Linked Polymer 0.06 g of the samples of condensate in Example 37, 90 mL concentrated hydrochloric acid and 10 mL ethylene glycol were placed in a one-neck round flask, stirred and heated to 20° C., completely degraded after 120 hours and transparent clear solution was obtained, which was neutralized with 95% sodium hydroxide solution and precipitated solid was filtered and the solid was washed with water and dried to give 0.058 g of degradation products of thermoset epoxy resin, mass recovery ratio was 95%.

Example 43: Degradation of Degradable Cross-Linked Polymer 0.57 g of the samples of condensate in Example 38, 10 mL concentrated hydrochloric acid and 90 mL ethylene glycol were placed in a one-neck round flask, stirred and heated to 190° C., completely degraded after 6 hours and transparent clear solution was obtained, which was neutralized with 50% sodium hydroxide solution and precipitated solid was filtered and the solid was washed with water and dried to give 0.54 g of degradation products of thermoset epoxy resin, mass recovery ratio was 95%.

Example 44: Degradation of Degradable Cross-Linked Polymer 0.6 g of the samples of condensate in Example 38, 10 mL concentrated hydrochloric acid and 45 mL phenylcarbinol were placed in a one-neck round flask, stirred and heated to 190° C., completely degraded after 6 hours and transparent clear solution was obtained, which was neutralized with 2% sodium hydroxide solution and precipitated solid was filtered and the solid was washed with water and dried to give 0.57 g of degradation products of thermoset epoxy resin, mass recovery ratio was 95%.

Example 45: Degradation of Degradable Cross-Linked Polymer 0.6 g of the samples of condensate in Example 38, 10 mL concentrated hydrochloric acid and 90 mL octanol were placed in a one-neck round flask, stirred and heated to 155° C., completely degraded after 4 hours and transparent clear solution was obtained, which was neutralized with 10% sodium hydroxide solution and precipitated solid was filtered and the solid was washed with water and dried to give 0.58 g of degradation products of thermoset epoxy resin, mass recovery ratio was 96%.

Example 46: Degradation of Degradable Cross-Linked Polymer 0.7 g of the samples of condensate in Example 38, 10 mL concentrated hydrochloric acid and 90 mL hexanol were placed in a one-neck round flask, stirred and heated to 155° C., completely degraded after 4 hours and transparent clear solution was obtained, which was neutralized with 20% sodium hydroxide solution and precipitated solid was filtered and the solid was washed with water and dried to give 0.66 g of degradation products of thermoset epoxy resin, mass recovery ratio was 95%.

Example 47: Degradation of Degradable Cross-Linked Polymer 0.55 g of the samples of condensate in Example 39, 10 mL concentrated hydrochloric acid and 90 mL hexanol were placed in a one-neck round flask, stirred and heated to 135° C., completely degraded after 6 hours and transparent clear solution was obtained, which was neutralized with 50% sodium hydroxide solution and precipitated solid was filtered and the solid was washed with water and dried to give 0.52 g of degradation products of thermoset epoxy resin, mass recovery ratio was 94%.

Example 48: Degradation of Degradable Cross-Linked Polymer 0.57 g of the samples of condensate in Example 8, 5 mL methanesulfonic acid and 90 mL hexanol were placed in a one-neck round flask, stirred and heated to 135° C., completely degraded after 6 hours and transparent clear solution was obtained, which was neutralized with 10% sodium hydroxide solution and precipitated solid was filtered and the solid was washed with water and dried to give 0.54 g of degradation products of thermoset epoxy resin, mass recovery ratio was 95%.

Example 49: Degradation of Degradable Cross-Linked Polymer 0.58 g of the samples of condensate in Example 39, 5 mL methanesulfonic acid and 90 mL ethanediol were placed in a one-neck round flask, stirred and heated to 135° C., completely degraded after 6 hours and transparent clear solution was obtained, which was neutralized with 0.1% sodium hydroxide solution and precipitated solid was filtered and the solid was washed with water and dried to give 0.57 g of degradation products of thermoset epoxy resin, mass recovery ratio was 98%.

Example 50: Degradation of Degradable Cross-Linked Polymer 0.55 g of the samples of condensate in Example 39, 5 mL methanesulfonic acid and 90 mL octanol were placed in a one-neck round flask, stirred and heated to 135° C., completely degraded after 6 hours and transparent clear solution was obtained, which was neutralized with 90% sodium hydroxide solution and precipitated solid was filtered and the solid was washed with water and dried to give 0.528 g of degradation products of thermoset epoxy resin, mass recovery ratio was 96%.

Example 51: Gel Time of Degradable Epoxy Matrix

At 100° C., the bisphenol A epoxy resin E51 (EEW 0.48~0.54 eq./100 g), E20 (EEW 0.18~0.22 eq./100 g) and E44 (EEW 0.41~0.47 eq./100 g) at a mass ratio of (3.5:5:1.5) were mixed and stirred uniformity, then cooled to 70° C., an equivalent amount of the curing agent 34 in Example 34 (AEW≈1.81 NH eq./100 g) was added and stirred at high speed evenly, the gel time of the resin mixture was more than 6 hours at 70° C.

At 70° C., the viscosity of the resin mixture was 20000-25000 cps. Similarly, the resin mixture was stored at −18° C. for 7 days and 30 days, the viscosity and gel time of the resin mixture had no significant change at 70° C. At 25° C. for 7 days and 30 days, the viscosity and gel time of the resin mixture had no significant change at 70° C.

Example 52: Gel Time of Degradable Epoxy Matrix

At 100° C., the bisphenol A epoxy resin E52D (EEW 0.52~0.54 eq./100 g), E20 (EEW 0.18~0.22 eq./100 g) and E44 (EEW 0.41~0.47 eq./100 g) at a mass ratio of (3.5:5:1.5) were mixed and stirred uniformity, then cooled to 70° C. and an equivalent amount of the curing agent 35 in Example 35 (AEW≈2.07 N—H eq./100 g) was added, and stirred at high speed evenly, the gel time of the resin mixture was more than 6 hours at 70° C.

At 70° C., the viscosity of the resin mixture was 20000-25000 cps. Similarly, the resin mixture was stored at −18° C. for 7 days and 30 days, the viscosity and gel time of the resin mixture had no significant change at 70° C. At 25° C. for 7 days and 30 days, the viscosity and gel time of the resin mixture had no significant change at 70° C.

Example 53: Preparation of Degradable Epoxy Resin Carbon Fiber Prepreg and Carbon Fiber Composite Laminate (1) Preparation of degradable epoxy matrix: 20 g bisphenol A epoxy resin E51 (EEW 0.48~0.54 eq./100 g) and 19 g the curing agent 34 in Example 34 (AEW≈1.81 NH eq./100 g) were weighed and mixed in a blender, then grinded in a three-roll mill for 30 minutes as standby. 15 g of a bisphenol A epoxy resin E51 (EEW 0.48~0.54 eq./100 g), 15 g bisphenol A epoxy resin E44 (EEW 0.41~0.47 eq./100 g) and 50 g bisphenol A epoxy E20 (EEW 0.18~0.22 eq./100 g), were placed in an oven preheated 120° C. for 3 hours, then put into a kneader to knead for 1 hour, cooled to 70° C., then the resin was put into mixing blender, then vacurated, at 70° C., former standby E51/curing agent 34 mixture system which was grinded in the three-roll grinding machine was added, then the resin mixture was stirred at high speed for 30 minutes, discharged, and cooled to room temperature, then frozen in store.

Above prepared degradable epoxy matrix, the gel time was more than 4 hours at 70° C., at room temperature, can be preserved more than a month, at 0° C., can be preserved more than half a year, at −18° C., can be preserved more than a year (2) preparation of degradable epoxy carbon fiber prepreg and carbon fiber composite laminate: The above prepared epoxy system was heated to 70° C., and carbon fiber prepreg was made using 3K carbon fiber cloth by wet method. The prepregs were slightly tacky at room temperatuer and pressed on the tablet pressing machine at 150° C. to give laminate of carbon fiber composite.

Example 54: Preparation of Degradable Epoxy Resin Uni-Direction Carbon Fiber Prepreg and Carbon Fiber Composite Laminate (1) Preparation of degradable epoxy matrix: 20 g bisphenol A epoxy resin E52D (EEW 0.52~0.54 eq./100 g) and 17 g the curing agent IV in Example 4 (AEW≈2.07 N—H eq./100 g) were weighed and mixed in a blender, then grinded in a three-roll mill for 30 minutes as standby. 15 g of a bisphenol A epoxy resin E52D (EEW 0.52~0.54 eq./100 g), 15 g bisphenol A epoxy resin E44 (EEW 0.41~0.47 eq./100 g) and 50 g bisphenol A epoxy E20 (EEW 0.18~0.22 eq./100 g), were placed in an oven preheated 120° C. for 3 hours, then put into a kneader to knead for 1 hour, cooled to 70° C., then the resin was put into mixing blender, then vacurated at 70° C., former standby E52/curing agent 34 mixture system which was grinded in the three-roll grinding machine was added, then the resin mixture was stirred at high speed for 30 minutes, discharged, and cooled to room temperature, then frozen in store.

Above prepared degradable epoxy matrix, the gel time is more than 4 hours at 70° C., at room temperature, can be preserved more than a month, at 0° C., can be preserved more than half a year, at −18° C., can be preserved more than a year.

(2) preparation of degradable epoxy uni-direction carbon fiber prepreg and carbon fiber composite laminate: The above prepared epoxy system was heated to 70° C., and carbon fiber prepreg was made using 3K carbon fiber cloth by wet method, the prepreg was slightly tacky at room temperature and pressed on the tablet pressing machine at 150° C. to give laminate of carbon fiber composite.

Example 55: Degradation of the Carbon Fiber Composite Laminate 1 g of the samples of the carbon fiber composite sheet in Example 53, 10 mL concentrated hydrochloric acid and 90 mL phenylcarbinol were placed in a one-neck round bottom flask, stirred and heated to 190° C., epoxy resin matrix was completely degraded after 3 hours, filtered when the solution was hot, the carbon fiber and the degradation solution were separated, the solution was neutralized with 20% sodium hydroxide solution and precipitated solid was filtered and the solid was washed with water and dried to give 0.98 g of degradation products of thermoset epoxy resin, mass recovery ratio was 98%. The surface of recycled fiber was clean and basically no defect.

Example 56: Degradation of the Carbon Fiber Composite Laminate 1 g of the samples of the carbon fiber composite sheet in Example 53, 10 mL concentrated hydrochloric acid and 90 mL ethanediol were placed in a one-neck round bottom flask, stirred and heated to 160° C., epoxy resin matrix was completely degraded after 3 hours, filtered when the solution was hot, the carbon fiber and the degradation solution were separated, the solution was neutralized with 30% sodium hydroxide solution and precipitated solid was filtered and the solid was washed with water and dried to give 0.97 g of degradation products of thermoset epoxy resin, mass recovery ratio was 97%. The surface of recycled fiber was clean and basically no defect.

Example 57: Degradation of the Carbon Fiber Composite Laminate 1 g of the samples of the carbon fiber composite sheet in Example 53, 10 mL concentrated hydrochloric acid and 90 mL hexanol were placed in a one-neck round bottom flask, stirred and heated to 135° C., epoxy resin matrix was completely degraded after 4 hours, filtered when the solution was not cooled down, the carbon fiber and the degradation solution were separated, the solution was neutralized with 20% sodium hydroxide solution and precipitated solid was filtered and the solid was washed with water and dried to give 0.98 g of degradation products of thermoset epoxy resin, mass recovery ratio was 98%. The surface of recycled fiber was clean and basically no defect.

Example 58: Degradation of the Carbon Fiber Composite Laminate 1 g of the samples of the carbon fiber composite sheet in Example 53, 10 mL concentrated hydrochloric acid and 90 mL octanol were placed in a one-neck round flask, stirred and heated to 135° C., epoxy resin matrix was completely degraded after 4 hours, filtered when the solution was hot, the carbon fiber and the degradation solution were separated, the solution was neutralized with 40% sodium hydroxide solution and precipitated solid was filtered and the solid was washed with water and dried to give 0.96 g of degradation products of thermoset epoxy resin, mass recovery ratio was 96%. The surface of recycled fiber was clean and basically no defect.

Example 59: Degradation of the Carbon Fiber Composite Laminate 1 g of the samples of the carbon fiber composite sheet in Example 54, 10 mL concentrated hydrochloric acid and 90 mL ethanediol were placed in a one-neck round flask, stirred and heated to 135° C., epoxy resin matrix was completely degraded after 4 hours, filtered when the solution was hot, the carbon fiber and the degradation solution were separated, the solution was neutralized with 20% sodium hydroxide solution and precipitated solid was filtered and the solid was washed with water and dried to give 0.97 g of degradation products of thermosetepoxy resin, mass recovery ratio was 97%. The surface of recycled fiber was clean and basically no defect.

Example 60: Degradation of the Carbon Fiber Composite Sheet 1 g of the samples of the carbon fiber composite sheet in Example 54, 5 mL methanesulfonic acid and 90 mL ethanediol were placed in a one-neck round flask, stirred and heated to 190° C., epoxy resin matrix was completely degraded after 3 hours, filtered when the solution was hot, the carbon fiber and the degradation solution were separated, the solution was neutralized with 10% sodium hydroxide solution and precipitated solid was filtered and the solid was washed with water and dried to give 0.95 g of degradation products of thermoset epoxy resin, mass recovery ratio was 95%. The surface of recycled fiber was clean and basically no defect.

Example 61: Degradation of the Carbon Fiber Composite Sheet 1 g of the samples of the carbon fiber composite sheet in Example 54, 5 mL methanesulfonic acid and 90 mL octanol were placed in a one-neck round flask, stirred and heated to 160° C., epoxy resin matrix is completely degraded after 3 hours, filtered when the solution was hot, the carbon fiber and the degradation solution were separated, the solution was neutralized with 50% sodium hydroxide solution and precipitated solid was filtered and the solid was washed with water and dried to give 0.965 g of degradation products of thermoset epoxy resin, mass recovery ratio was 97%. The surface of recycled fiber was clean and basically no defect.

Example 62: Degradation of the Carbon Fiber Composite Sheet 1 g of the samples of the carbon fiber composite sheet in Example 54, 5 ml methanesulfonic acid and 90 mL hexanol were placed in a one-neck round flask, stirred and heated to 135° C., epoxy resin matrix was completely degraded after 4 hours, filtered when the solution was hot, the carbon fiber and the degradation solution were separated, the solution was neutralized with 20% sodium hydroxide solution and precipitated solid was filtered and the solid was washed with water and dried to give 0.9 g of degradation products of thermoset epoxy resin, mass recovery ratio was 95%. The surface of recycled fiber was clean and basically no defect.

Example 63: Degradation of the Carbon Fiber Composite Sheet 0.3 g of the samples of the carbon fiber composite sheet in Example 54, 0.1 mL concentrated hydrochloric acid and 90 mL ethanediol were placed in an autoclave, stirred and heated to 350° C., epoxy resin matrix was completely degraded after 0.5 hours, cool down to 100° C., filtered when the solution was not cooled down, the carbon fiber and the degradation solution were separated, the solution was neutralized with 0.1% sodium hydroxide solution and precipitated solid was filtered and the solid was washed with water and dried to give 0.285 g of degradation products of thermoset epoxy resin, mass recovery ratio was 95%.

Example 64: Degradation of the Carbon Fiber Composite Sheet 0.1 g of the samples of the carbon fiber composite sheet in Example 54, 90 mL concentrated hydrochloric acid and 2 mL ethanediol were placed in an autoclave, stirred at 20° C., filtered after 120 hours, the carbon fiber and the degradation solution were separated, the solution was neutralized with 100% sodium hydroxide solution and precipitated solid was filtered and the solid was washed with water and dried to give 0.095 g of degradation products of thermoset epoxy resin, mass recovery ratio was 95%.

What is claimed is:
1. A compound of Formula (I) or a salt thereof:

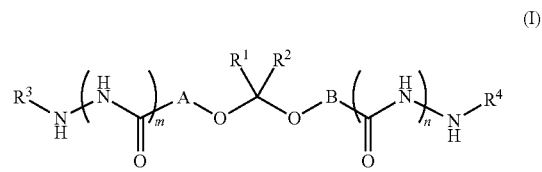

wherein:
each of $R^1$ and $R^2$, independently, is hydrogen, alkyl, cycloalkyl, heterocyclic, heterocycloalkyl, alkenyl, cycloalkenyl, aryl, heteroaryl, alkyl-hetero-alkyl, alkynyl, alkylene, alkylene-hetero-alkylene, alkenylene, alkylene-hetero-alkenylene, alkynylene, or alkylene-hetero-alkynylene; or, $R^1$ and $R^2$, together with the carbon atom to which they are attached, form a 3- to 7-membered saturated or unsaturated cyclic or heterocyclic ring containing 1 to 3 heteroatoms each independently being O, S, or NH;
each of A and B, independently, is alkylene, alkylene-hetero-alkylene, alkenylene, alkenylene-hetero-alkenylene, alkylene-hetero-alkenylene, alkynylene, cycloalkylene, alkylene-cycloalkylene, alkylene-cycloalkylene-alkylene, alkenylene-cycloalkylene, alkenylene cycloalkylene-alkenylene, alkylene-cycloalkylene-alkenylene, alkynylene-cycloalkylene, alkynylene-cycloalkylene-alkynylene, heterocycloalkylene, alkylene-heterocycloalkylene, alkylene-heterocycloalkylene-alkylene, alkenylene-heterocycloalkylene, alkenylene-heterocycloalkylene-alkenylene, alkylene-heterocycloalkylene-alkenylene, alkynylene-heterocycloalkylene, alkynylene-heterocycloalkylene-alkynylene, cycloalkenylene, alkylene-cycloalkenylene, alkylene-cycloalkenylene-alkylene, alkenylene-cycloalkenylene, alkenylene-cycloalkenylene-alkenylene, alkylene-cycloalkenylene-alkenylene, alkynylene-cycloalkenylene, alkynylene-cycloalkenylene-alkynylene, heterocycloalkenylene, alkylene-heterocycloalkenylene, alkylene-heterocycloalkenylene-alkylene, alkenylene-heterocycloalkenylene, alkenylene-heterocycloalkenylene-alkenylene, alkylene-heterocycloalkenylene-alkenylene, alkynylene-heterocycloalkenylene, alkynylene-heterocycloalkenylene-alkynylene, alkylene-arylene, alkylene-arylene-alkylene, alkenylene-arylene, alkenylene-arylene-alkenylene, alkylene-arylene-alkenylene, alkynylene-arylene, alkynylene-arylene-alkynylene, alkylene-hetero-arylene, alkylene-hetero-arylene-alkylene, alkenylene-hetero-arylene, alkenylene-hetero-arylene-alkenylene, alkylene-hetero-arylene-alkenylene, alkynylene-hetero-arylene, or alkynylene-hetero-arylene-alkynylene;

each of $R^3$ and $R^4$, independently, is hydrogen, alkyl, cycloalkyl, heterocyclic, heterocycloalkyl, alkenyl, cycloalkenyl, aryl, heteroaryl, alkoxyalkyl, or alkynyl; and both m and n are 1.

2. The compound of claim 1, wherein each of A and B, independently, is alkylene, alkenylene, alkylene-arylene, alkenylene-arylene, alkynylene-arylene, alkylene-hetero-arylene, alkenylene-hetero-arylene, or alkynylene-hetero-arylene.

3. The compound of claim 1, wherein each of A and B, independently, is alkylene.

4. The compound of claim 3, wherein both A and B are, at the same time, alkylene.

5. The compound of claim 4, wherein both A and B are, at the same time, methylene or ethylene.

6. The compound of claim 1, wherein each of $R^1$ and $R^2$, independently, is hydrogen, alkyl, cycloalkyl, heterocyclic, heterocycloalkyl, alkenyl, cycloalkenyl, aryl, heteroaryl, alkyl-hetero-alkyl, alkynyl, alkylene, alkylene-hetero-alkylene, alkenylene, alkylene-hetero-alkenylene, alkynylene, or alkylene-hetero-alkynylene; or $R^1$ and $R^2$, together with the carbon atom to which they are attached, form a 3- to 7-membered saturated or unsaturated ring.

7. The compound of claim 6, wherein each of $R^1$ and $R^2$, independently, is hydrogen or alkyl, or $R^1$ and $R^2$, together with the carbon atom to which they are attached, form a 3- to 7-membered saturated ring.

8. The compound of claim 7, wherein each of $R^1$ and $R^2$, independently, is hydrogen, methyl, or ethyl.

9. The compound of claim 1, wherein each of $R^3$ and $R^4$, independently, is hydrogen or alkyl.

10. The compound of claim 9, wherein each of $R^3$ and $R^4$, independently, is hydrogen, methyl, ethyl, propyl, or isopropyl.

11. The compound of claim 1, wherein the compound is

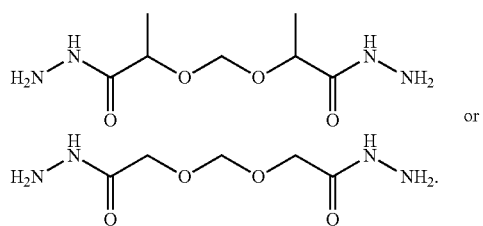

12. The compound of claim 1, wherein the compound is a salt formed with an organic acid or Lewis acid.

13. The compound of claim 12, wherein organic acid is a $C_{1-10}$ aliphatic, cycloaliphatic, aromatic, or heteroaromatic carboxylic acid.

14. The compound of claim 12, wherein the compound is a salt of oxalic acid, citric acid, or zinc chloride.

15. A degradable cross-linked polymer, wherein the polymer is synthesized by curing an epoxy resin with a compound of claim 1, the epoxy resin comprises a glycidyl ether epoxy resin, glycidyl ester epoxy resin, glycidyl amine epoxy resin, trifunctional epoxy resin, tetrafunctional epoxy resin, novolac epoxy resin, cresol-novolac epoxy resin, aliphatic epoxy resin, alicyclic epoxy resin, or nitrogen-containing epoxy resin.

16. A method for degrading degradable cross-linked polymer of claim 15, comprising the steps of:
(1) under the condition of heating and stirring, the cross-linked polymer is immersed in a mixture comprising an acid and a solvent, the mixture is heated to a temperature in the range of 15-400° C., the heating time is 1-120 hours, and the mass concentration of acid in the solvent is 0.1-100%;
(2) using an alkaline solution of 0-200° C. to adjust the pH value of the mixture of acid and solvent to at least 6, the mass concentration of alkali solution is 0.1-100%.

17. The method of claim 16, wherein the acid comprises hydrochloric acid, hydrobromic acid, hydrofluoric acid, acetic acid, trifluoroacetic acid, lactic acid, formic acid, propionic acid, citric acid, methanesulfonic acid, p-toluenesulfonic acid, nitric acid, sulfuric acid, sulfurous acid, phosphoric acid, perchloric acid, benzoic acid, salicylic acid, or phthalic acid; and the solvent comprises methanol, ethanol, ethylene glycol, propanol, isopropanol, butanol, isobutanol, t-butanol, pentanol, hexanol, heptanol, octanol, nonanol, benzyl alcohol, phenethyl alcohol, p-hydroxymethyl benzene, m-hydroxymethyl benzene, o-hydroxy benzene, p-hydroxyethyl benzene, m-hydroxyethyl benzene, o-hydroxyethyl benzene, water, N,N-dimethylformamide, N,N-dimethylacetamide, N-methylpyrrolidone, dimethyl sulfoxide, tetrahydrofuran, methyl tetrahydrofuran, glycerol, or dioxane; the alkali comprises lithium hydroxide, sodium hydroxide, potassium hydroxide, calcium hydroxide, sodium carbonate, sodium bicarbonate, potassium carbonate, potassium bicarbonate, ammonia; the alkali solvent comprises methanol, ethanol, ethylene glycol, propanol, isopropanol, butanol, isobutanol, t-butanol, pentanol, hexanol, heptanol, octanol, nonanol, water, N, N-dimethylformamide, N, N-dimethylacetamide, N-methylpyrrolidone, dimethyl sulfoxide, tetrahydrofuran, methyl tetrahydrofuran, glycerol, or dioxane.

18. The method of claim 17, wherein in step (1), the heating temperature is 80-150° C., heating time is 4-8 hours, and the mass concentration of acid in the solvent is 0.5-20%; in step (2) the temperature is 5-50° C., the pH value is adjusted to the range of 6-12, the concentration of alkali solution is 5-30%.

19. A prepreg material or a reinforced composite material, wherein the material is derived from a compound of claim 1, an epoxy resin, an optional auxiliary material, and a reinforcing material; the epoxy resin comprises a glycidyl ether epoxy resin, glycidyl ester epoxy resins, glycidyl amine epoxy resin, trifunctional epoxy resin, tetrafunctional epoxy resin, novolac epoxy resin, o-cresol novolac epoxy resin, aliphatic epoxy resin, alicyclic epoxy resin, or nitrogen-containing epoxy resin; the reinforcing material comprise carbon nanotubes, boron nitride nanotubes, carbon black, metal nano-particles, metal oxide nanoparticles, organic nanoparticles, iron oxide, glass fibers, carbon fibers, natural fibers, synthetic fibers, or a fabric made up by fiber material; and the optional auxiliary material comprise an accelerator, diluent, plasticizer, toughening agent, thickening agent, coupling agent, defoamer, flatting agent, ultraviolet absorber, antioxidant, brightener, fluorescent agent, pigment, or filler.

20. A method for preparing a compound of Formula (I) of claim 1, wherein both $R^3$ and $R^4$ are hydrogen, comprising the following reaction scheme:

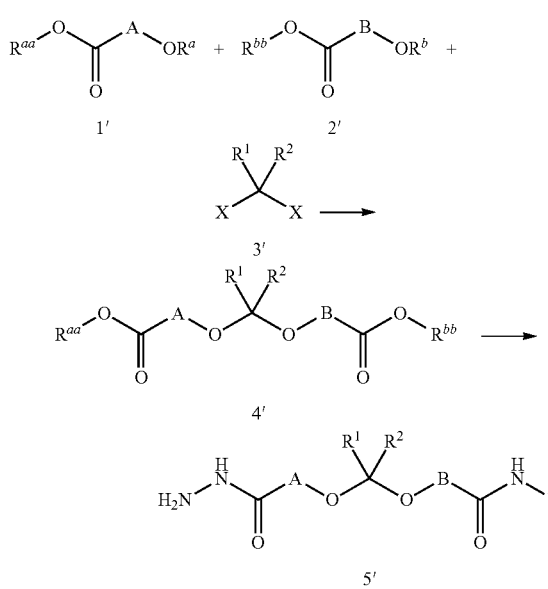

A, B, $R^1$, and $R^2$ are as defined in claim 1, each X independently is a halogen atom, or both X groups together form =O;

each of $R^{aa}$ and $R^{bb}$, independently, is alkyl, cycloalkyl, heterocycle, heterocycloalkyl, alkenyl, cycloalkenyl, aryl, heteroaryl, alkyl-hetero-alkyl, or alkynyl;

each of $R^a$ and $R^b$, independently, is hydrogen, alkali metal, alkaline earth metal, or quaternary ammonium salt;

when each X independently is a halogen atom, intermediate compound 4' reacts with hydrazine in a second organic solvent at a temperature in the range of 0-150° C. to produce compound 5'; and when both X groups together form =O, intermediate compound 4' reacts with hydrazine in a second organic solvent at a temperature in the range of 0-150° C. to produce compound 5'.

21. The method of claim 20, wherein the second organic solvent comprises methanol, ethanol, propanol, isopropanol, butanol, isobutanol, t-butanol, pentanol, hexanol, heptanol, octanol, nonanol, decanol, dioxane, tetrahydrofuran, or ethylene glycol; and the hydrazine comprises anhydrous hydrazine or hydrazine hydrate.

22. The method of claim 20, wherein each X independently is a halogen atom, compounds 1', 2', and 3' react in a first organic solvent at a temperature in the range of 30-200° C. to produce intermediate 4', the molar ratio of compounds 1' and 2' is not higher than 10:1, and the molar ratio of the compounds 1' and 2' versus compound 3' is not higher than 100:1.

23. The method of claim 22, wherein the first solvent comprises tetrahydrofuran or dioxane.

24. The method of claim 20, wherein both X groups together form =O, and both $R^a$ and $R^b$ are hydrogen.

25. The method of claim 24, wherein compounds 1', 2', and 3' react in a first organic solvent in the presence of a catalyst at a temperature in the range of 30-200° C. to produce intermediate 4', the molar ratio of compounds 1' and 2' is not higher than 10:1, and the molar ratio of the compounds 1' and 2' versus compound 3' is not higher than 100:1.

26. The method of claim 25, wherein the catalyst comprises p-toluenesulfonic acid, pyridinium p-toluenesulfonic acid, sulfuric acid, phosphoric acid, nitric acid, hydrogen chloride, molecular sieves, sulfonic acid resin, or solid super acid.

* * * * *